(12) United States Patent
Seesselberg et al.

(10) Patent No.: US 8,459,795 B2
(45) Date of Patent: Jun. 11, 2013

(54) MEASURING SYSTEM FOR OPHTHALMIC SURGERY

(75) Inventors: Markus Seesselberg, Aalen (DE); Peter Reimer, Ellwangen (DE); Christoph Hauger, Aalen (DE); Christoph Kuebler, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 259 days.

(21) Appl. No.: 13/049,708

(22) Filed: Mar. 16, 2011

(65) Prior Publication Data

US 2012/0069303 A1 Mar. 22, 2012

Related U.S. Application Data

(63) Continuation-in-part of application No. PCT/EP2009/006690, filed on Sep. 16, 2009.

(51) Int. Cl.
*A61B 3/10* (2006.01)

(52) U.S. Cl.
USPC .......................................... 351/221; 351/205

(58) Field of Classification Search
USPC .................................................. 351/205, 221
See application file for complete search history.

(56) References Cited

U.S. PATENT DOCUMENTS

| 6,212,006 B1 | 4/2001 | Reiner |
| 6,409,345 B1 | 6/2002 | Molebny et al. |
| 6,486,943 B1 | 11/2002 | Burns et al. |
| 6,550,917 B1 | 4/2003 | Neal et al. |
| 6,736,510 B1 | 5/2004 | Van Heugten |
| 2003/0078753 A1 | 4/2003 | Campin et al. |
| 2005/0241653 A1 | 11/2005 | Van Heugten et al. |
| 2006/0152677 A1 | 7/2006 | Youssefi et al. |
| 2007/0013918 A1 | 1/2007 | Hauger et al. |
| 2007/0229760 A1 | 10/2007 | Hirohara et al. |
| 2008/0117503 A1 | 5/2008 | Reimer et al. |
| 2008/0117504 A1 | 5/2008 | Reimer et al. |
| 2008/0304144 A1 | 12/2008 | Reimer et al. |
| 2009/0257065 A1 | 10/2009 | Hauger et al. |
| 2010/0309478 A1 | 12/2010 | Reimer et al. |

FOREIGN PATENT DOCUMENTS

| DE | 299 05 969 U1 | 8/1999 |
| DE | 199 50 792 A1 | 4/2001 |
| DE | 103 04 222 A1 | 8/2004 |
| DE | 103 60 570 A1 | 7/2005 |
| DE | 10 2005 031 496 B4 | 1/2007 |
| EP | 1 332 712 A1 | 8/2003 |

(Continued)

OTHER PUBLICATIONS

Cornejo-Rodriguez, A., "Ronchi Test", in: "Optical Shop Testing", Ed. by D. Malacara, John Wiley & Sons, Inc., 1978, pp. 283-322.

(Continued)

*Primary Examiner* — Jack Dinh
(74) *Attorney, Agent, or Firm* — Potomac Patent Group, PLLC

(57) ABSTRACT

The invention relates to an optical measuring system comprising a wave front sensor for characterizing a shape of a wave front of measuring light and an imaging lens, wherein the imaging lens comprises a first optical assembly and a second optical assembly for imaging an object region in an entrance region of the wave front sensor. A distance between the object region and the first optical assembly is larger than a focal length of the first optical assembly. Furthermore, the optical measuring system can comprise an optical microscopy system and optionally an OCT system for carrying out different optical examination methods at the same time.

35 Claims, 11 Drawing Sheets

FOREIGN PATENT DOCUMENTS

| | | |
|---|---|---|
| WO | WO 91/01703 | 2/1991 |
| WO | WO 91/01703 A1 | 2/1991 |
| WO | WO 01/58339 A2 | 8/2001 |
| WO | WO 02/25347 A2 | 3/2002 |
| WO | WO 2008/115060 A1 | 9/2008 |

OTHER PUBLICATIONS

Ghozeil, I., "Hartmann and Other Screen Tests", in: "Optical Shop Testing", Ed. by D. Malacara, John Wiley & Sons, Inc., 1978, pp. 323-349.

Liang, J. et al., "Objective measurement of wave aberrations of the human eye with the use of a Hartmann-Shack wave-front sensor", J. Opt. Soc. Am. A, vol. 11, No. 7, Jul. 1994, pp. 1949-1957.

Malacara, D., "Basic Interferometers", in: Handbook of Optical Engineering, Ed. by D. Malacara & B. J. Thompson, Marcel Dekker, Inc., 2001, pp. 339-371.

Pang, L. et al., "Set of two orthogonal adaptive cylindrical lenses in a monolith elastomer device", Optics Express, vol. 13, No. 22, 2005, pp. 9003-9013.

Xu, Y. et al., "MEMS based non-rotatory circumferential scanning optical probe for endoscopic optical coherence tomography", Proc. of SPIE, vol. 6627, 2007.

Office Action in counterpart German patent application No. 10 2008 047 400.2 dated Apr. 24, 2009, 6 pages.

MEASURING SYSTEM FOR OPHTHALMIC SURGERY

CROSS-REFERENCES TO RELATED APPLICATIONS

This application claims priority to and is a continuation-in-part of International Patent Application No. PCT/EP2009/006690, filed Sep. 16, 2009, which claims priority to German Patent Application No. DE 10 2008 047 400.2, filed Sep. 16, 2008, the disclosures of which are hereby incorporated by reference in their entirety.

BACKGROUND OF THE INVENTION

The present invention relates to a measuring system for ophthalmic surgery having a wavefront sensor and imaging optics. In particular, the invention relates to a measuring system for ophthalmic surgery having a wavefront sensor and imaging optics and which is suitable for use in surgery, in particular for use in eye surgery, by providing a sufficiently large distance between the imaging optics and the object under inspection. Furthermore, the invention relates to a measuring system for ophthalmic surgery having a wavefront sensor and an OCT system.

Wavefront sensors, which are configured to characterize the form of a wavefront of measuring light, are known in the art. Such wavefront sensors may in particular be used to measure aberrations of a human eye by using a Hartmann-Shack sensor, as described in the article of J. Liang, B. Grimm, S. Goelz, J. F. Bille, "Objective measurement of a Hartmann-Shack wavefront sensor", J. Opt. Soc. Am. A 11 (1994) pp. 1949-1957. In such a system, the Hartmann-Shack sensor comprises in particular an array of microlenses which is arranged in a plane, wherein in a common focal plane of the microlenses, a position-sensitive light sensor is arranged. With such a Hartmann-Shack sensor, a form of a wavefront, which is incident onto the array of microlenses may be determined by measuring local inclinations of a wavefront in regions corresponding to each of the microlenses.

For measuring the optical properties of a human eye, an illumination spot, which is as small as possible, is generated on the retina of the human eye. A nearly spherical wave emanates from this point-like illumination spot, traverses the vitreous body, the lens and the cornea and leaves the human eye. The form of the wavefront is altered when it traverses the different optical interfaces of the human eye. This results in a deviation of the exiting wavefront from a plane wavefront. These deviations from a plane wavefront may be represented by local inclinations within a lateral region and thereby may be measured by using a Hartmann-Shack wavefront sensor.

Document US 2005/0241653 A1 discloses a wavefront sensor which can be arranged and mounted between an objective lens of a microscope system and an object under inspection.

Document U.S. Pat. No. 6,550,917 B1 discloses a wavefront sensor, which is designed such that a spherical wavefront is transformable into a plane wavefront. The spherical wavefront may for example be a wavefront, which exits an ametropic eye having a spherical aberration. Thereby, it is possible to increase a measuring range of the wavefront sensor.

The document DE 103 60 570 B4 discloses an optical measuring system, which comprises an OCT-system and a wavefront analysis system. Based on a measurement of a form of a wavefront, an adaptive optical element is controlled such that wavefronts, which are measured by a wavefront detector are substantially plane wavefronts. Thereby, it is possible to obtain an improved OCT signal.

However, the wavefront sensors, which are disclosed in the documents mentioned above are only of limited use in surgical operations, since they require a short distance between the object and the optical component which is located closest to the object.

Therefore, it is an object to provide an optical measurement system having a wavefront sensor and which is suitable for use in surgical operations. In particular, it is an object to provide a measuring system having a wavefront sensor and which is suitable for use in eye surgery, in particular cataract surgery.

It is a further object to provide an optical measuring system having a wavefront sensor and an OCT system and which allows to inspect an object by analyzing wavefronts, which emanate from the object, wherein the analysis is performed by measuring a three-dimensional structure data set. The measuring system further has to be suitable for surgical operations.

SUMMARY OF THE INVENTION

The present invention has been accomplished taking the above problems into consideration.

Embodiments provide an optical measuring system, or a measuring system for eye surgery, which provides the surgeon with sufficient working space to perform surgical operations.

According to an embodiment, there is provided an optical measuring system, which comprises a wavefront sensor for characterizing a form of a wavefront of measuring light in an entry region of the wavefront sensor; and imaging optics having a first optical assembly and a second optical assembly for imaging an object region onto the entry region of the wavefront sensor by using the measuring light, wherein the following relation holds:

$1.1 * f \leq d$, wherein f denotes a focal distance of the first optical assembly; and
d denotes a distance between the object region and the first optical assembly.

The wavefront sensor may comprise an extensive array of refractive or diffractive optical elements. The array of optical elements may be an array of microlenses. Each of these refractive or diffractive optical elements may be designed such that the measuring light is focused in a focal plane. In a common focal plane, which is formed from the individual focal planes of the refractive or diffractive optical elements, there may be provided a position-sensitive light sensor. The position-sensitive light sensor may for example be a CCD camera and/or a CMOS sensor or any other light sensitive sensor. The position-sensitive light sensor may be configured to resolve a spatial intensity distribution. The position-sensitive light detector may be arranged in a plane, which is oriented perpendicular to an optical axis of the wavefront sensor. The entry region of the wavefront sensor may be defined by a region, in which the array of refractive or diffractive optical elements is arranged. This region may have the form of a plane. This plane may for example be defined by fitting a plane to optical interfaces of the refractive or diffractive optical elements, wherein the optical interfaces comprise those optical surfaces of the wavefront sensor, which are located furthest away from the position-sensitive light sensor.

Depending on a form of a wavefront of measuring light, which is incident on the wavefront sensor, light ray bundles of this wavefront are imaged onto a corresponding array of regions on the position sensitive light detector by the array of refractive or diffractive optical elements. These regions of the focused light ray bundles may have the form of an ellipse or a circle. An average position or a position of a center of mass of each of the regions relative to a lateral position of the corresponding refractive or diffractive optical elements is indicative of a local inclination or tilt of the light ray bundle of the respective refractive or diffractive optical element, wherein the wavefront, which is incident on the wavefront sensor comprises this light ray bundle.

The position-sensitive light sensor may comprise a plurality of sensor segments or pixels. Depending on a light intensity, which is incident on each of the detector segments, electrical signals are generated by the wavefront sensor. Then, these electrical signals are transmitted to a processing unit. The processing unit is configured to determine from the electrical signals a position of the focused light ray bundles. The position may be a position of the center or center of mass, for example as a center of mass of a region, which extends over several detector segments and which is formed by an incident focused bundle of light rays, which has traversed one of the refractive or diffractive optical elements of the wavefront sensor.

According to embodiments, the wavefront sensor is a Hartmann-Shack sensor. Alternatively, the wavefront sensor may for example be an interferometer, a classic Hartmann-Test, a Ronchi test, Talbot interferometry, or a phase retrieval method. Furthermore, the optical measuring system may be configured such that a possible astigmatic aberration of the eye of the patient is pre-compensated by a variable cylindrical lens. The cylindrical lens may be rotatably supported. For example, the cylindrical lens may be a liquid lens.

The optical measuring system may further comprise a light source for illuminating an object under inspection. The measuring system may be configured to illuminate a region of the retina of the eye under inspection, wherein the region is as small as possible. A wavefront of measuring light, which is substantially parallel or spherical may be incident on the eye under inspection, and after the wavefront has traversed the cornea, the lens and the vitreous body of the eye under inspection, the wavefront is incident on the retina as a substantially spherical wavefront. Thereby, a region of the retina is illuminated, which has a small extent. Depending on an ametropia of the eye under inspection, this region may have the form of a circle or an ellipse. The difference between the length of the major axes of the ellipse may increase with the astigmatic aberration of the eye under inspection.

In order to measure the form of a wavefront which is emanating from an eye under inspection, the wavefront is directed onto the entry region of the wavefront sensor. For this purpose, the optical measuring system comprises imaging optics having a first optical assembly and a second optical assembly. The optical assemblies may comprise one or a combination of the following: refractive optical elements, diffractive optical elements, such as mirrors and/or lenses and/or gratings, and/or one or more electronically or mechanically controllable variable lenses or mirrors, which may be designed such that their optical refractive power is adaptable by varying their shape. Optical components of an optical assembly may have a fixed position relative to each other, such as cemented elements, or alternatively, individual lenses and/or cemented elements, which are mounted using lens mounts.

By traversing the first optical assembly, light, which emanates from a point in the focal region of the first optical assembly into different directions is transformed into a bundle of light, which is consists of substantially parallel light rays. By this fact, a position of the focal region of the first optical assembly is determinable. The focal region may have the form of a plane, which is located perpendicular to an optical axis of the first optical assembly. In this case, the focal region may be referred to as the focal plane. The focal point of the first optical assembly may be defined as the point, where the optical axis of the first optical assembly intersects the focal plane. An incident ray of light, which passes through the focal point of the first optical assembly and which forms a small angle with the optical axis, is transformed by the first optical assembly into an outgoing light beam, which runs parallel to the optical axis of the first optical assembly. A point of intersection of the extended outgoing light beam with the extended incident light beam is located in the principal plane of the first optical assembly. The focal length f of the first optical assembly is defined by the distance between the principal plane of the first optical assembly and the focal plane of the first optical assembly.

The distance d between the object region and the first optical assembly is defined by a distance between the object region and an optical surface of a component of the first optical assembly, wherein this optical surface may represent an optical surface of components of the first optical assembly, which is located closest to the object region along a beam path of the measuring light. This component of the first optical assembly is an optical component having the effect of a lens, i.e. a component which has a refractive power of greater than zero. For example, this component is not a plane-parallel plate or any other form of a component which does not modify a form of a wavefront of measuring light. Hence, further optical components may be arranged in the beam path of measuring light between the object region and the first optical assembly at a distance from the object region, which is smaller than d. These further optical components may have a refractive power of zero or a refractive power which is small compared to the refractive power of the first optical component, such as smaller than 5% or smaller than 1% of the refractive power of the first optical assembly. The refractive power of the first optical assembly is given by the reciprocal of the focal length, i.e. by 1/f.

The distance d thereby represents a free space between the first optical assembly and the object under inspection. This free space is sometimes referred to as working space and the distance d is sometimes referred to as working distance. By fulfilling the condition $1.1*f \leq d$, it is ensured that the working distance d is greater than the focal length f of the first optical assembly. An increase in d thereby leads to an increase of the working distance, which ma be advantageous in surgical operations such as in surgical operations performed on the human eye.

Moreover, the range of focal lengths of the first optical assembly is limited by various constraints. One of such constraints is the magnification, which is necessary to image a region having the diameter of the pupil of the eye onto the entry region of the wavefront sensor. A further constraint is a total length of the imaging optics, which typically should be designed compact in size. Therefore, it is typically not possible to increase the focal length of the first optical assembly until a sufficient working distance is achieved. Consequently, it is advantageous to have an measuring system for ophthalmic surgery, which fulfills the condition $1.1*f \leq d$.

According to an embodiment, $1.5*f \leq d$ holds, or $1.75*f \leq d$ holds, or $2*f \leq d$ holds. For particular applications, it is advantageous, to provide a comparatively small focal length of the first optical assembly. Also in this case, a sufficiently large working distance can be attained for conducting surgical operations.

According to an embodiment, $d \geq 150$ millimeters holds, or $d \geq 175$ millimeters holds, or $d \geq 190$ millimeters holds. Such working distances allow to conduct surgical operations under a variety of requirements, such as requirements, which result from conducting eye surgery. According to further embodiments, $d \leq 500$ millimeters holds, or $d \leq 300$ millimeters holds, or $d \leq 200$ millimeters holds.

According to an embodiment, at least one of the first optical assembly and the second optical assembly is a refractive optical assembly, such as for example a lens assembly. A lens assembly is a set of lenses, which comprises one or more lenses. A lens assembly may consist of cemented elements. Lenses of a lens assembly may be arranged at a fixed position relative to each other.

According to an embodiment, the optical measuring system further comprises a third optical assembly, which is arranged and configured to image the object region along a beam path of the microscope onto an image region, which is different from the entry region of the wavefront sensor. The image region may be located at a distance from the entry region of the wavefront sensor. Thereby, it is possible to perform optical microscopy of the object region in addition to performing an analysis of the wavefront. Performing optical microscopy may be helpful during conducting surgical operations.

According to an embodiment, the object region is located at a focal region of the first optical assembly.

According to an embodiment, the first optical assembly comprises a first optical subassembly and a second optical subassembly, which are located at a distance from each other. The first optical assembly consists of the first optical subassembly and the second optical subassembly. By way of example, the first optical subassembly and the second optical subassembly are arranged at a fixed position relative to each other.

According to an embodiment, an optical path, which is traversed by the measuring light along the beam path of the measuring light between the first optical assembly and the second optical assembly, is adaptable. The adaptability of the optical path has the advantage that a spherical aberration of a human eye under inspection is pre-compensatable. Thereby, it is possible to minimize a curvature of the wavefront, which is incident on the wavefront sensor and thereby to increase a measuring range or a dynamic range of the wavefront sensor. In case the wavefront of measuring light has a spherical form when being incident on the first optical assembly, the wavefronts in the entry region of the wavefront sensor may be transformed into wavefronts having a substantially plane form. This transformation may be adapted by increasing or decreasing the optical path between the first optical assembly and the second optical assembly, by increasing or decreasing the optical path between the second optical subassembly of the first optical assembly and the second optical assembly.

Even when varying the optical path between the first optical assembly and the second optical assembly, the focal region of the first optical assembly which may consist of the first optical subassembly and the second optical subassembly, is still imaged onto the entry region of the wavefront sensor. The varying of the optical path may comprise moving/displacing the second optical subassembly relative to the second optical assembly. In other words, the second optical subassembly may be configured such that it is displaceable or movable relative to the second optical assembly. There may be provided an actuator for varying the optical path, wherein the actuator is designed to provide a driving force for displacing or moving the second optical subassembly relative to the second optical assembly. The actuator may be a motor or an actuator, which may be configured to transmit a driving force for the displacement, such as an actuation mechanism like a screw. The displacement may be performed along a track or guide. An amount of the displacement, such as a distance of the displacement, may be detected and measured by a detector. The actuator may be in signal communication with a controller, such that the controller may activate the actuator. The controller may comprise or make use of a calibration curve, which allows to convert between the amount of a spherical aberration of the eye under inspection and a distance of a displacement for pre-compensating this ametropia. By using the calibration curve, it is possible to control the actuator for displacing the second optical subassembly relative to the second optical assembly based on a known ametropia of the eye under inspection.

According to an embodiment, the measuring system for ophthalmic surgery is configured to characterize a form of a wavefront of measuring light, which emanates from an eye, which is arranged in an object region, wherein the eye has a spherical aberration of between −5 dpt (diopters) to +25 dpt (diopters), by varying the optical path between the first optical assembly and the second optical assembly. The sign of the spherical aberration of the eye is defined such that an aphakic eye, i.e. an eye with the natural lens removed, has a spherical aberration of about +20 dpt.

According to an embodiment, the optical measuring system further comprises a reflector for deflecting the measuring light, for example by 180°, wherein the reflector is displaceably arranged between the first optical assembly and the second optical assembly in the beam path of the measuring light for varying the optical path traversed by the measuring light. By way of example, the reflector is displaceably arranged between the second optical subassembly of the first optical assembly and the second optical assembly in the beam path of the measuring light.

According to an embodiment, the reflector comprises at least two mirror surfaces, which are arranged at an angle different from zero. In other words, the two mirror surfaces are arranged at an angle relative to each other, which is different from zero. The reflector may for example comprise two or three mirrors, wherein the reflector does not comprise any further reflecting surfaces. It is advantageous to use exactly two mirrors due to the favourable polarization behavior.

According to an embodiment, the optical measuring system further comprises a retroreflector, which is arranged between the first optical assembly (for example the second optical subassembly of the first optical assembly) and the second optical assembly in the beam path of the measuring light. A retroreflector is an optical system, which substantially reverses a propagation direction of the measuring light. This feature is substantially independent from an orientation of a propagation direction of the measuring light relative to the retroreflector. By way of example, the measuring light is not reflected by the retroreflector along the beam path of the incident measuring light, but along a path, which is laterally displaced relative to the beam path of the incident measuring light. In other words, the reflected path of measuring light, which is outgoing from the retroreflector is parallel to and located at a distance from the path of measuring light which is incoming onto the retroreflector. By arranging a retroreflector between the second optical subassembly and the second optical assembly, it is possible to vary the optical path between the second optical subassembly and the second optical assembly by displacing the retroreflector. A displacement of the retroreflector in a direction parallel to the optical axis of the first optical assembly by a distance 1 results in an increase or decrease of the optical path between the second optical subassembly and the second optical assembly by 2*n*1, wherein n denotes a refractive index of a medium within the beam path of the measuring light between the second optical subassembly and the second optical assembly. Providing the retroreflector allows to design the optical measuring system very compact in size. This in turn allows the optical measuring system to be mounted within or beneath a microscope system.

According to an embodiment, the retroreflector comprises a corner cube. A corner cube comprises a transparent body, which substantially has a form of a three-sided pyramid. The three-sided pyramid may comprise three triangles which are oriented perpendicular to each other, each of which being in the form of an isosceles, right-angled triangle, and further a surface in the form of an equilateral triangle. With this corner cube, an incident light beam is reflected by the corner cube at three surfaces. The mirroring process may result from total internal reflection. However, it is also conceivable, that a reflective coating is applied to the surfaces at which a mirroring process occurs, for example by applying a metallic coating. Thereby, a possible polarization of the light is influenced in a different way.

According to an embodiment, the optical measuring system further comprises a beam splitter, which is arranged between the entry region of the wavefront sensor and the second optical assembly. The beam splitter may be designed as a polarization beam splitter. The beam splitter may advantageously be used for coupling measuring light into the beam path. Hence, the measuring light on the way from the beam splitter to the object in the focal region of the first optical assembly traverses substantially the same path as the light, which emanates from the object on the way to the beam splitter. On the way from the beam splitter to the object, the measuring light traverses the second optical assembly and the first optical assembly (for example the first optical subassembly and the second optical subassembly of the first optical assembly). On the way from the object to the beam splitter, the measuring light traverses the first optical assembly (for example the first optical subassembly and the second optical subassembly of the first optical assembly) and the second optical assembly. Furthermore, the measuring light reaches the wavefront sensor along a portion of the beam path, which is not traversed by the measuring light on the way from the beam splitter to the object. Thereby, it is for example ensured, that in the case of an eye under inspection, which has a spherical aberration, the measuring light, which illuminates the eye, is adaptable with respect of a curvature of the wavefront of the measuring light, such that the illumination spot on the retina of the eye under inspection is as small as possible. This may be performed by varying the optical path between the second optical assembly and the second optical subassembly.

According to an embodiment, the following relation holds: $d(1,2) \geq f1*d/(d-f1)$, wherein $d(1,2)$ represents a distance between components of the first optical subassembly and components of the second optical subassembly and f1 represents a focal length of the first optical subassembly. The first optical subassembly and the second optical subassembly are located for example along the optical axis of the first optical assembly at a distance from each other, such that light beams, which emanate from a point in the focal region of the first optical assembly, intersect between the first optical subassembly and the second optical subassembly after having traversed the first optical subassembly. In a region of such an intersection, an intermediate image of the object region which is arranged in the focal region of the first optical assembly may be formed. $d(1,2)$ represents a distance along an optical axis of the first optical assembly between an optical surface of a component of the first optical subassembly and an optical surface of a component of the second optical subassembly, wherein both components have an optical power different from zero and wherein both optical components are those optical components of the first and second optical subassembly, respectively, which have the smallest distance from each other.

According to an embodiment, the first optical subassembly comprises a fist lens group, which may comprise or consist of an objective lens; and he first optical subassembly further comprises a second lens group, which is arranged at a distance from the first lens group, wherein the microscope beam path traverses the first lens group of the first optical subassembly and wherein the third optical assembly comprises a zoom system. Thereby, the beam path of the measuring light for the wavefront sensor as well as the microscope beam path traverses the first lens group of the first optical subassembly. Thereby, it is possible to provide an optical measuring system, which allows to perform an analysis of the wavefront and at the same time optical microscopy, wherein the first lens group of the first optical subassembly is used for both purposes. Thereby, it is possible, to provide an integration of the components of the optical measuring system, which is compact in size.

According to an embodiment, a mirror surface, such as a mirror surface of a folding mirror is arranged in the beam path of the measuring light between the first lens group and the second lens group of the first optical subassembly. The mirror surface is provided for spatially separating the beam path of the measuring light from the microscopy beam path.

According to an embodiment, the second lens group of the first optical subassembly and the second optical subassembly form an afocal system. The measuring system may comprise an afocal system, which consists of the second lens group of the first optical subassembly and the second optical subassembly. The afocal system may be a Kepler telescope. By traversing an afocal system, light, which consists of plane wavefronts is transformed into light which also consists of plane wavefronts. A Kepler telescope is an optical system which consists of two lenses or lens systems. The two lenses or lens systems are arranged at a distance from each other along the optical axis, wherein the distance may correspond to the sum of the focal lengths of both lenses or lens systems.

According to an embodiment, the object region is located in a focal region of the first lens group of the first optical subassembly. The first lens group of the first optical subassembly may be referred to as a main objective lens of a microscopy system. Hence, the object region is located in the focal region of the main objective lens of the microscopy system. This is advantageous in case further optical components are used downstream of the main objective lens, such as a zoom system or an eye-piece.

According to an embodiment, the third optical assembly comprises an objective lens and a zoom system, wherein the beam path of the measuring light is free from traversals of the objective lens and wherein a mirror surface is arranged in the beam path of the measuring light between the object region and the first optical subassembly. In other words, the beam path of the measuring light does not traverse the objective lens. According to this embodiment, none of the components of the optical measuring system, mentioned so far, are provided for an analysis of the wavefront and for conducting optical microscopy. This may have the advantage that the components for an analysis of the wavefront may be designed such that they are detachably mountable on an optical microscopy system and hence may be dismounted for performing an analysis of the wavefront. Furthermore, the components may be designed such that they are mountable on different optical microscopy systems without requiring significant optical components of the optical microscopy system or without having to adapt significant optical components of the optical microscopy system.

According to an embodiment, the object region is located in a focal region of the objective lens.

According to an embodiment, the object region is different from a focal region of the first optical assembly. The object region may be located at a distance from the focal region of the first optical assembly.

According to an embodiment, the first optical assembly and the second optical assembly together form an afocal system, such as for example a Kepler telescope. The measuring system comprises an afocal system, which consists of the first optical assembly and the second optical assembly.

According to an embodiment, a beam splitter is displaceably arranged between the first optical assembly and the second optical assembly in the beam path of the measuring light. Through the beam splitter, illumination light is directable to the object region. For example, the measuring system may comprise an actuator, which is attached to the beam splitter, and which is configured to displace the beam splitter upon receiving control signals from a control unit of the measuring system.

According to an embodiment, a mirror surface is arranged between the first optical assembly and the object region. Thereby, the optical measuring system is combinable with a microscopy system, wherein the beam splitter decouples from the light, which is used for microscopy a portion, which forms the measuring light for wavefront analysis.

According to an embodiment, the measuring system for ophthalmic surgery further comprises an OCT system having an OCT light source for generating an OCT measuring light, wherein in a beam path of the OCT measuring light between the first optical assembly and the second optical assembly or between the second optical assembly and the entry region of the wavefront sensor, there is arranged an OCT beam splitter such that OCT measuring light is directed to at least the first optical assembly for illuminating the object region. In case the OCT beam splitter is arranged between the first optical assembly and the second optical assembly, the OCT measuring light is directed only through the first optical assembly and not through the second optical assembly for illuminating the object region. In case the OCT beam splitter is arranged between the second optical assembly and the entry region of the wavefront sensor, the OCT measuring light traverses the first optical assembly as well as the second optical assembly for illuminating the object region. The OCT measuring light may interact with the OCT beam splitter, wherein the interacting may for example comprise a transmitting or reflecting. The OCT beam splitter may be configured to arrange the beam path of the OCT measuring light such that it is identical, at least in a portion thereof, with the beam path of the measuring light, which is used for an analysis of the wavefront. Thereby, the measuring light, which is used for the analysis of the wavefront may traverse or be reflected by components of the system which are also traversed by OCT measuring light or at which also OCT measuring light is reflected, wherein the optical components of the system may comprise the first optical assembly. Additionally, the components may also comprise the second optical assembly. Thereby, a set-up, which is cost-effective and compact in size may be obtained.

Optical coherence tomography (OCT) is a method based on interferometry for obtaining structural information of an object in a volumetric portion by reflecting light at different depths of an object under examination.

The OCT light source may be configured to provide OCT measuring light having wavelengths in the visible and/or near infrared range of wavelengths, wherein a bandwidth of the OCT light source is adjusted such that a coherence length of the OCT measuring light, which is emitted from the OCT light source, is between several micrometers and several tenths of micrometers. A portion of the OCT measuring light, which is emitted from the OCT light source is guided along an OCT beam path which comprises mirrors, lenses and/or fiber optics to an object, which is located in the object region. The OCT measuring light penetrates into the object, depending on the wavelengths and the material within the object, to a certain penetration depth. A portion of the penetrated OCT measuring light is reflected depending on a reflectivity within the object and is superimposed on a second portion of OCT measuring light, which has been emitted from the OCT light source and which has been reflected at a reference surface. The superimposed light is detected by a detector and converted into electrical signals, which correspond to an intensity of the detected superimposed light. Due to a comparatively short coherence length of the OCT measuring light, constructive interference is only observed when a difference between the optical path which has been traveled by the OCT measuring light to and back from the object and the optical path which has been traveled by the second portion of the light, which has been emitted by the OCT light source and has been reflected by the reference surface, is less than the coherence length of the OCT measuring light.

Different embodiments provide different variants of an OCT system. The different variants of the OCT system are different from each other in the way, structural information is obtained from a scanning along a depth direction (axial direction) as well in the way the superimposed light is detected. According to an embodiment of a time domain OCT (TD-OCT), the reference surface, at which the second portion of light, which has been emitted by the light source, is reflected, is displaced for obtaining structural information of the object from different depths. In this case, an intensity of the superimposed light may be detected by a photo detector.

In Frequency-Domain-OCT (FD-OCT), the second portion of the OCT measuring light, which is emitted by the OCT light source is also reflected at a reference surface. However, the reference surface does not have to be displaced for obtaining structural information from different depths within the object. Rather, superimposed light is spectrally dispersed into spectral portions by a spectrometer, wherein the spectral portions are detected for example by a position sensitive detector, such as a CCD camera. Through a Fourier-Transform of the obtained spectrum of the superimposed light, structural information of the object along the depth direction is obtainable (Fourier-Domain-OCT).

Further variants of FD-OCT is Swept-Source-OCT (SS-OCT). A spectrum of superimposed light is sequentially recorded by continuously varying a mean wavelength of OCT measuring light having a very narrow band width. At the same time, the superimposed light is recorded by using a photo diode.

The OCT system may for example be used to inspect the structure of an anterior chamber or posterior chamber of the human eye, or the retina of the human eye.

According to an embodiment, the measuring system for ophthalmic surgery further comprises at least one scanning mirror, which is pivotably arranged between the OCT light source and the OCT beam splitter for scanning the OCT measuring light over the object region. The OCT system may further comprise collimating optics for collimating OCT measuring light, which is generated by the OCT light source.

By pivoting the at least one scanning mirror, the collimated OCT measuring light may be guided as a focused OCT measuring beam over the object region. Thereby, structural information may be obtained from a laterally extended portion of the object region. The system may comprise more than one scanning mirror, such as two scanning mirrors, which are pivotable about different axes.

According to an embodiment, the at least one scanning mirror, the second lens group of the first optical subassembly and the second optical subassembly are configured and arranged to image a region close to the at least one scanning mirror onto a region close to the mirror surface. The first optical assembly comprises, as described above, the first optical subassembly and the second optical subassembly, wherein the first optical subassembly comprises a second lens group. The second lens group of the first optical subassembly and the second optical subassembly may form an afocal system for imaging a region which is located close to the scanning mirror to a region, which is located close to the mirror surface.

A detailed description of the design and arrangement of the scanning mirrors, the mirror surface and how the region close to the at least one scanning mirror is imaged onto the region close to the mirror surface by the first optical subassembly and the second optical subassembly is given in US 2009/0257065, the whole contents of which is incorporated herein by reference in its entirety.

The mirror surface is arranged between the first lens group of the first optical subassembly and the second lens group of the first optical subassembly in the beam path of the measuring light for analyzing a wavefront. The mirror surface, which is for example part of a folding mirror may reflect the measuring light such that it traverses a further lens such as an objective lens of a microscope on the path to the object region. For an optimal adjusted system, a center of the at least one scanning mirror is imaged onto a center of the mirror surface by the second lens group of the first optical subassembly and by the second optical subassembly. Such an optical imaging process has the advantage that for different pivoting positions of the at least one scanning mirror, the OCT measuring light which emanates from a point on the scanning mirror is imaged onto a point in the center of the mirror surface, i.e. without beam walk-off. Thereby, it is prevented that the OCT measuring light fails to impinge on the mirror surface. Hence, it is possible to design the mirror surface comparatively compact in size.

In case the system comprises two scanning mirrors, which are arranged at a distance from each other, the system may be designed and adjusted such that the point in the middle of a connecting line between the two scanning mirrors is imaged onto a center of the mirror surface, or at least onto a region which is located close to the mirror surface, such as onto a region, which is located along the OCT beam path at a distance from the center of the mirror surface at most 100 times, 10 times or 2 times of the lateral extent of the mirror surface. The lateral extent of the mirror surface may be a diameter of the mirror surface. The connecting line may be oriented along the OCT beam path of the optical system, which consists of the second lens group of the first optical subassembly and the second optical subassembly. A distance of the region from the mirror surface may depend on an optical magnification of the system, which consists of the second lens group of the first optical subassembly and the second optical subassembly, such that the distance increases with a higher magnification. This dependence may be linear.

A region, which is located close to the scanning mirror may comprise spatial points, which have a distance to the scanning mirrors of the system, which is smaller, for example smaller by a factor of 10, or smaller by a factor of 5 or smaller by a factor of 2, as an extent one of the scanning mirrors, which the system comprises. The extent of the scanning mirror may be a diameter of the scanning mirror.

A region close to the mirror surface may comprise spatial points which have a distance to the mirror surface, which is smaller in particular by a factor of 10, by a factor of 5 or by a factor of 2, as an extent of the mirror surface. The distance may be measured along the OCT beam path. The mirror surface and the OCT beam path may form an angle of between 30° and 60°. The extent of the mirror surface may for example be a diameter of the mirror surface.

According to an embodiment, the measuring system for ophthalmic surgery further comprises a wavefront light source for generating measuring light which is used for analyzing the wavefront, wherein at least 80% of a total intensity of the generated measuring light consists of light having wavelengths of between 800 nm and 870 nm, or of between 820 nm and 840 nm. In other words, at least 80% of a total intensity of the generated measuring lights consists of wavelengths of between 800 nm and 870 nm, or of between 820 nm and 840 nm. The measuring light may for example be generated by a superluminescence diode (SLD). Measuring light of such a wavelength is in particular suitable to traverse the human eye until the retina such that it forms an illumination spot on the retina. Then, after diffuse reflection, the light leaves the eye and is inspected in view of its form of the wavefront by the wavefront sensor. It is advantageous to use light of these wavelength ranges, since this light is not perceived by the eye of the patient, such that the patient is not blinded and the iris of the eye of the patient does not contract. A contracted iris would impair the measurement.

According to an embodiment, at least 80% of a total intensity of the generated OCT measuring light consists of light having wavelengths between 1280 nm and 1320 nm, or of between 1300 nm and 1320 nm. OCT measuring light of these wavelengths is in particular suitable to enter a region of the interior chamber of the eye and being reflected by this region. Thereby, structural information from the anterior chamber may be obtained. Moreover, it is possible to obtain structural information from the posterior chamber of the eye and/or the retina.

For examining or observing the retina by OCT, a wavelength range between 800 nm and 870 nm is well suitable, since this light reaches the retina. In this case, spectra of the wavefront light source and the OCT light source may overlap such that at least 60%, or at least 80% of an intensity of the measuring light for the analysis of the wavefront is located in a wavelength range, in which 80% of an intensity of the OCT measuring light is located. The measuring light for the analysis of the wavefront may comprise essentially the same wavelengths as the OCT measuring light. In this case, it is possible to use a single light source which generates the measuring light for the analysis of the wavefront and also the OCT measuring light.

According to an embodiment, a least 60%, or at least 80% of a total intensity of the measuring light consists of wavelengths, which define a wavelength range of measuring light, in which at least 80% of a total intensity of the OCT measuring light is located.

In other words, a spectral intensity distribution of the measuring light and a spectral intensity distribution of the OCT measuring light are configured such that in an overlapping wavelength range of these intensity distributions, at least 60% or at least 80% of a total intensity of the measuring light is located and at least 80% of a total intensity of the OCT measuring light is located.

According to embodiments, at least 70%, or at least 90% of the intensities of the measuring light, which is used for the wavefront analysis and the OCT measuring light are not located in overlapping wavelength ranges. In other words, at least 70%, or at least 90% of a total intensity of a spectral intensity distribution is not located in an overlapping wavelength range of the spectral intensity distribution of the measuring light and the spectral intensity distribution of the OCT measuring light. Although, the measuring light, which is used for the wavefront analysis, and the OCT measuring light traverse or interact with optical components of the measuring system for ophthalmic surgery, those measuring lights may be separated from each other, for example by dichroic elements, due to their different wavelength ranges. The optical components, with which the measuring lights interact or which are traversed by the measuring lights, may for example be the first optical assembly and optionally also the second optical assembly. Thereby, it is prevented that a measurement of the wavefront influences a measurement with the OCT-system. However, both measuring lights may comprise common wavelength ranges and their spectra may overlap to a large extent.

According to an embodiment, the OCT beam splitter comprises a dichroic mirror, wherein a transmission of the dichroic mirror in a wavelength range of between 800 nm and 870 nm, or of between 820 nm and 840 nm is at least twice as high or at most half as high as the transmission in a wavelength range of between 1280 nm and 1340 nm or of between 1300 nm and 1320 nm.

According to embodiments, at least 80% of an intensity of the measuring light for wavefront analysis or of the OCT measuring light is transmitted through the OCT beam splitter.

According to an embodiment, the OCT beam splitter comprises a dichroic mirror, wherein a reflectivity of the dichroic mirror in a wavelength range of between 1280 nm and 1340 nm, or of between 1300 nm and 1320 nm is at least twice as high or at most half as high as a reflectivity in a wavelength range of between 800 nm and 870 nm, or of between 820 nm and 840 nm.

According to an embodiment, at least 80% of an intensity of the measuring light for wavefront analysis or of the OCT measuring light is reflected by the OCT beam splitter.

The dichroic mirror may be coated with layers of materials having different dielectric constants. These layers may be configured such that constructive interference is generated for the reflected measuring light or the transmitted measuring light in case the measuring light impinges onto the dichroic mirror.

According to an embodiment, a major part, or at least 70% of an intensity of OCT measuring light which impinges onto the OCT beam splitter is reflected at the OCT beam splitter. Additionally or alternatively, a major part, or at least 70% of an intensity of measuring light for wavefront analysis, which impinges onto the OCT beam splitter, is transmitted through the OCT beam splitter.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF THE INVENTION

Figure 1A:
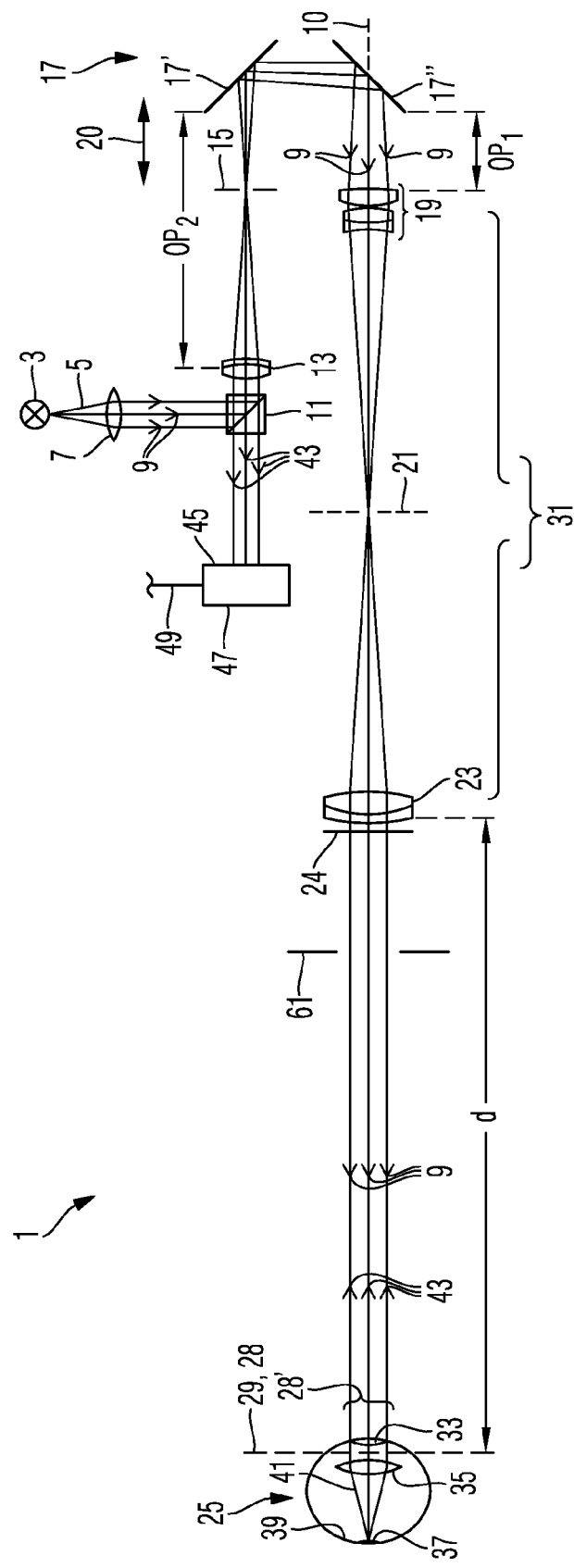
FIG. 1A schematically illustrates an embodiment of an optical measuring system, wherein an illumination beam path or wavefront beam path, respectively, is illustrated.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1A schematically illustrates an optical measuring system 1 according to an embodiment. Measuring system 1 comprises a light source 3, which generates measuring light 5. Measuring light 5 is collimated by collimating optics 7 for generating measuring light 9, which substantially consists of plane wavefronts. Measuring light 9 is reflected at the beam splitter 11 and traverses cemented element 13. The measuring light, which is converged by cemented element 13 passes through aperture 15 and is deflected by 180° by reflector 17 which comprises two mirror surfaces 17' and 17", which are oriented orthogonal to each other. Thereby, measuring light 9 is deflected in a substantially reverse direction and displaced in a lateral direction, i.e. in a direction which is perpendicular to a propagation direction of the measuring light 9.

In further embodiments, the reflector 17 may be a corner cube. The corner cube comprises a body made of glass, having the form of a three-sided pyramid. The outer surfaces of the pyramid consists of isosceles, right-angled triangles, wherein each pair of these triangles is oriented perpendicular to each other. Furthermore, the corner cube comprises a basis surface, which is in the form of an equilateral triangle. In case the corner cube is used in the measuring system, the measuring light 9 is reflected at the three isosceles, right-angled, triangular surfaces.

The reflector 17 is displaceable in directions which are denoted by the double arrow 20. The aperture 15 is arranged in a focal region of the cemented element 13, wherein the position of the cemented element is independent of a displacement position of the reflector 17.

The measuring light 9, which is reflected by the reflector 17, traverses a cemented element 19, whereby convergent measuring light is formed. In the plane 21, the measuring light 9 is substantially converged to a point, a crossover, and continues as a divergent measuring light. The divergent measuring light 9 traverses a further cemented element 23 and is transformed into plane wavefronts. The plane measuring light 9 traverses a quarter wave plate 24 and impinges onto an eye 25 in the form of a plane wavefront. The pupil of the human eye 25 is located in the object plane 28. The image of the iris is referred to as the pupil of the eye 25. Typically, the pupil is located about 2.7 to 3 mm behind the vertex of the cornea 33. In this embodiment, the object plane 28 is located at the focal plane 29 of the first optical assembly 31, which consists of the cemented element 23 and the cemented element 19. Hence, the pupil of the eye 25 is located in the focal plane 29.

The reflector 17 may be configured to be displaceable or movable along a direction, which is parallel to the optical axis of the first optical assembly (31) and/or the optical axis of the second optical assembly (13). In particular, the reflector may be configured such that it is displaceable or movable forward and backward parallel to the optical axis of the first optical assembly (31) and/or the optical axis of the second optical assembly (13).

Measuring light 9 traverses the cornea 33 and the lens 35 of the eye 25, and is focused onto a spot 37 on the retina 39. At the beam splitter 11, the measuring light consists of plane wavefronts, i.e. of a bundle of parallel light ray beams. Measuring light is imaged onto a spot 37 on the retina of the eye 25 when the optical components are at a fixed position relative to each other only in case of an emmetropic eye having no spherical aberration. In this case, the reflector is positioned such that the total system consisting of the three optical assemblies 23, 19 and 13 is an afocal system. However, in case the eye has a spherical aberration, it is possible to displace the reflector 17 or the corner cube 17, respectively, along a direction, which is indicated by double arrow 20, for generating slightly convergent measuring light 9 or slightly diverging light 9, which is incident on the eye 25. Thereby, it is possible, even in case the eye has a spherical aberration, to generate an illumination spot of the measuring light on the retina, which is as small as possible. By displacing the corner cube 17 along a direction, which is indicated by double arrow 20, an optical path of the measuring light between the cemented element 13 and the cemented element 19 is varied. Therefore, in case of a spherical aberration of the eye 25 being within a certain range, measuring light 9 is focusable on a point on the retina 39 of the ametropic eye 25.

The illumination spot 37 is a diffuse light source on the retina 39 of the eye 25 which emits light 41, which consists of substantially spherical wavefronts. Light 41 traverses the vitreous body, the lens 35 and the cornea 33 and forms light 43. Depending on optical properties and the shape of the lens 35 and the cornea 33, a wavefront of the light 43 deviates from a plane wavefront. The form of the wavefronts, which form light 43, is indicative of an ametropia of the optical components or the interfaces of the eye 25, i.e. for example of the optical properties and the form of the lens 35 and the cornea 33.

Light 43 traverses cemented element 23 and forms convergent light. In a spatial region of the plane 21, in which an image of the retina is formed, light 43 is converged to a minimum extent and thereafter diverges. Furthermore, measuring light 43 traverses cemented element 19, is reflected and laterally displaced by reflector 17, passes aperture 15, traverses cemented element 13 and forms light, which substantially consists of plane wavefronts. A deviation of the wavefronts of the measuring light 43 from plane wavefronts is indicative of an ametropia of the eye 25.

Figure 1B:
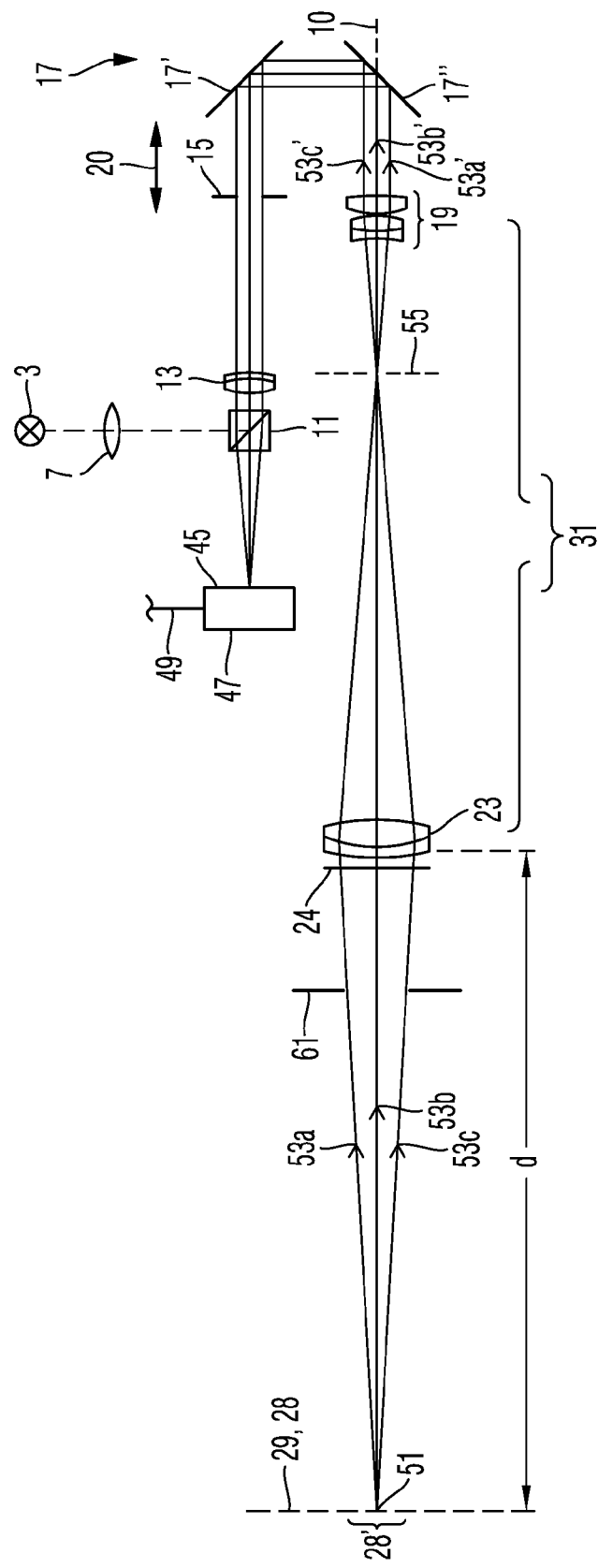
FIG. 1B schematically illustrates the embodiment, which is illustrated in FIG. 1A, wherein an object beam path is illustrated.

Measuring light 43 enters the entry region 45 of a Hartmann-Shack sensor 47. The entry region 45 is formed by an array of microlenses, wherein in a common focal plane of the microlenses, an electronic imaging sensor such as a chip of a CCD camera is arranged. The electronic imaging sensor comprises a plurality of pixels, each of which converts intensity values of incident light into electrical signals. The electrical signals are transmitted via data line 49 to a processing unit, which is not illustrated. For each of the microlenses of the array of microlenses of the Hartmann-Shack sensors 47, the processing unit determines a displacement position of the light, which is focused by the respective microlens. Thereby, a form of a wavefront of the measuring light 43 in the entry region 45 of the Hartmann-Shack sensor is determinable. With reference to FIG. 1B, it is described, that a region of the focal plane 29 is imaged onto the entry region 45 of the Hartmann-Shack sensor 47. Thereby, a form of a wavefront of light 43, which is emitted from the eye 25 is determinable. With reference to FIG. 1B, further properties and advantages of the optical measuring system 1 are described. The pupil of the eye 25 in the object plane 28 is arranged in the focal plane 29 of the first optical assembly 31, which consists of the cemented elements 23 and 19. Three light beams 53a, 53b, 53c, emanate from a focal point 53 in the focal plane 29 along the object beam path, traverse the quarter wave plate 24 and the cemented element 23 and are converged to a minimum extent in an intermediate image region 55. Beams 53 emanate from the intermediate image region 55 as divergent beams, traverse cemented element 19 and exit the cemented element 19 as substantially parallel beams 53a', 53b', 53c'. The parallel beams 53a', 53b', 53c' are reflected and laterally displaced by reflector 17, pass the aperture 15, traverse cemented element 13 and are focused to a point after having traversed the beam splitter 11. This point is defined by the optical axis of the measuring system 1 and the entry region 45 of the Hartmann-Shack sensor 47. Thereby, a point in the focal plane 29 is imaged onto a point in the entry region 45 of the Hartmann-Shack sensor 47. Displacement of the corner cube 17 along a direction, which is indicated by double arrow 20 does not modify this imaging properties, since light beams, which emanate from a point in the focal plane 29 are oriented parallel between cemented element 19 and cemented element 13, where the reflector 17 is arranged in the beam path. Hence, a form of a wavefront, which exits from an ametropic or emmetropic eye may be inspected with high precision.

Figure 1C:
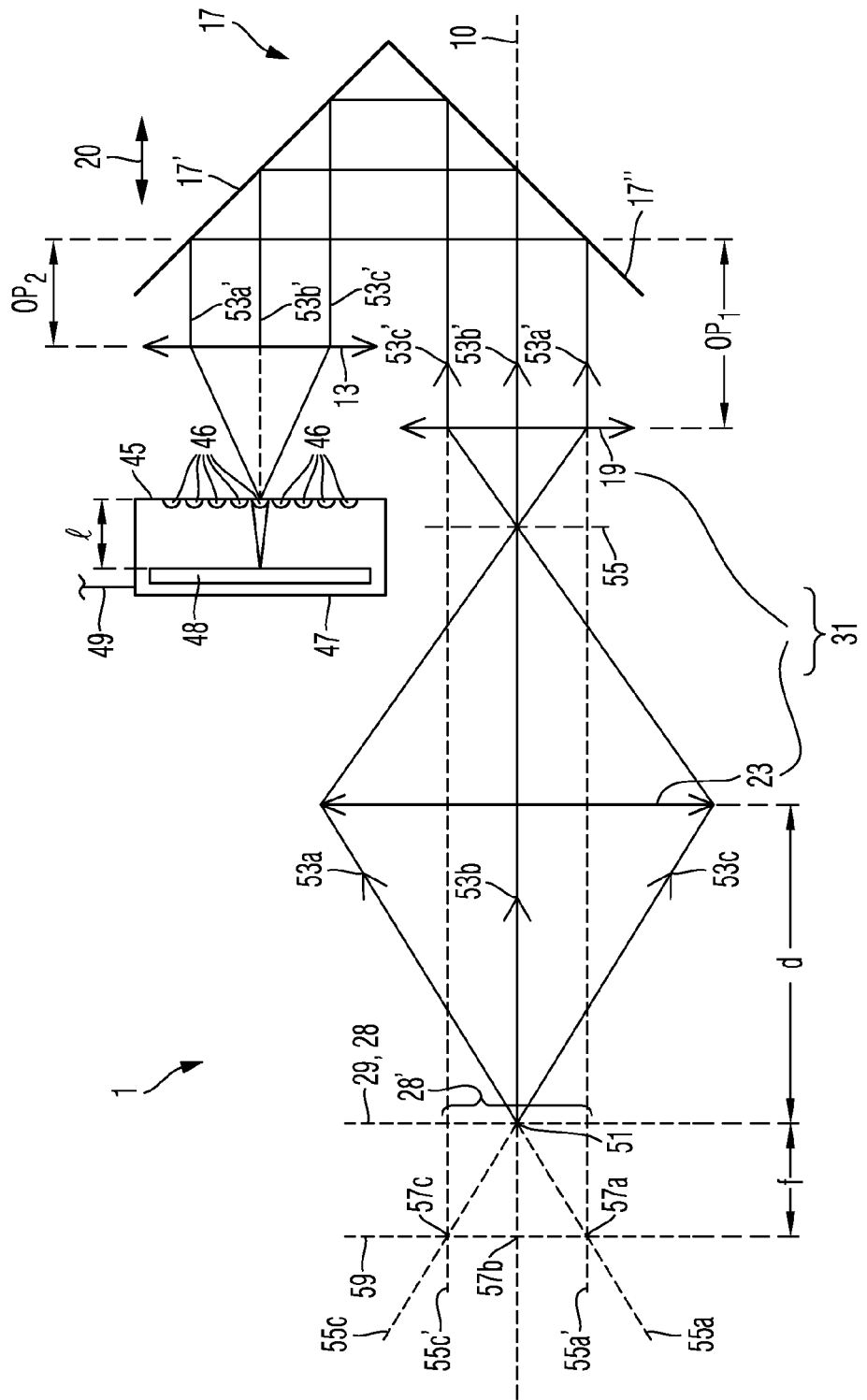
FIG. 1C schematically illustrates a section of the embodiment illustrated in FIGS. 1A and 1B of an optical measuring system.

FIG. 1C schematically illustrates a portion of the optical measuring system 1 of the schematically illustrated embodiment of FIGS. 1A and 1B. The light beams 53a, 53b and 53c emanate from the focal point 51, traverse cemented element 23 and are focused onto the intermediate image region 55. From the intermediate image region 55, three light beams emanate and are deflected by cemented element 19 such that three parallel light beams 53a', 53b' and 53c' are formed, which run parallel to the optical axis 10. Cemented elements 23 and 19 form the first optical assembly 31, as described above. A focal length f of the first optical assembly 31 may be determined as described in the following:

The light beam 53a', which is parallel to the optical axis 10 is extended in a direction towards the focal plane 29 and beyond the focal plane 29 such as illustrated by dashed line

55a'. Accordingly, the light beam 53b, which is incident on the first optical assembly 31 and which is transformed into beam 53a' after having traversed the optical system 31, is extended beyond focal plane 29, such as illustrated by dashed line 55a. The line 55a and the line 55a' intersect in a point 57a. The point 57a is located in a principal plane 59 of the first optical assembly 31. The principal plane 59 is located at a distance f away from the focal plane 29, which is parallel to the principal plane 59. In the principal plane, there is also located point 57c, which is analog to point 57a, wherein the point 57c is defined by the intersection of lines 55c' and 55c. Hence, light beams 53a and 53c appear to be refracted at points 57a or 57c, respectively, which are located in the principal plane 59. After having traversed the first optical assembly 31, light beams 53a and 53c run parallel to the optical axis.

The light beams 53a', 53b' and 53c' are reflected by corner cube 17, as schematically illustrated, and are focused by cemented element 13 onto the entry region 45 of the wavefront sensor 47. The entry region 45 is formed by those surfaces of the microlenses 46, which are located closest to the cemented element 13. An object region 28' in the object plane 28 in the focal plane 29 of the first optical assembly 31 is therefore imaged onto the entry region 45 of the wavefront sensor 47. Each of the microlenses 46 has a focal length 1. At a distance 1 from the entry region 45 of the wavefront sensor 47, there is arranged a CCD 48 for a position sensitive detection of light intensities. As described above, a detection of a distribution of light intensities and an analysis thereafter allows to determine a form of a wavefront of the measuring light, which emanates from the object region 28'. The object region 28' in the focal plane 29 of the first optical assembly 31 is located at a distance d away from an optical surface of the first optical assembly 31, wherein this optical surface is the optical surface which is closest to the focal region 29. In the exemplary embodiment, which is illustrated, the distance d is about 2.5 times the focal length f of the first optical assembly 31.

The optical measuring system 1 is especially suited for eye surgery, such as for example cataract surgery. The cornea or the pupil of the eye under surgery is arranged at the object region 28'. The distance d between the cornea or the pupil of the eye under inspection and a component of the first optical assembly 31 is 220 mm in the exemplary embodiment 1. Hence, the surgeon has enough working space for performing surgical operations with his hands.

The embodiment 1 of an optical measuring system, as illustrated in FIGS. 1A, 1B and 1C, may be mounted at a fixed position relative to an optical microscopy system. For example, the optical measuring system is supported upstream of the objective lens of the optical microscopy system in a beam path of measuring light which emanates from the object under inspection. In this embodiment, measuring light 43, which emanates from the object region 28', may be reflected by a folding mirror 61, which is schematically indicated. After reflection at the folding mirror 61, the measuring light is incident on the entry region 45 of the wavefront sensor 47 after having traversed the first optical assembly 31 and being reflected at the corner cube 17 and having traversed the cemented element 13. In FIGS. 1A and 1B, the position of the folding mirror 61 is indicated. Another part of the light, which emanates from the object region 28' is guided through an objective lens of the microscopy system for performing microscopic imaging. Therefore, it is possible for a surgeon to obtain a microscopic image of an object under surgery as well as to conduct an analysis of a form of a wavefront of measuring light, which emanates from the object region 28'. According to embodiments, the folding mirror 61 is located close to the objective lens of the microscopy system. Thereby, a free working space is reduced as little as possible.

Figure 2A:
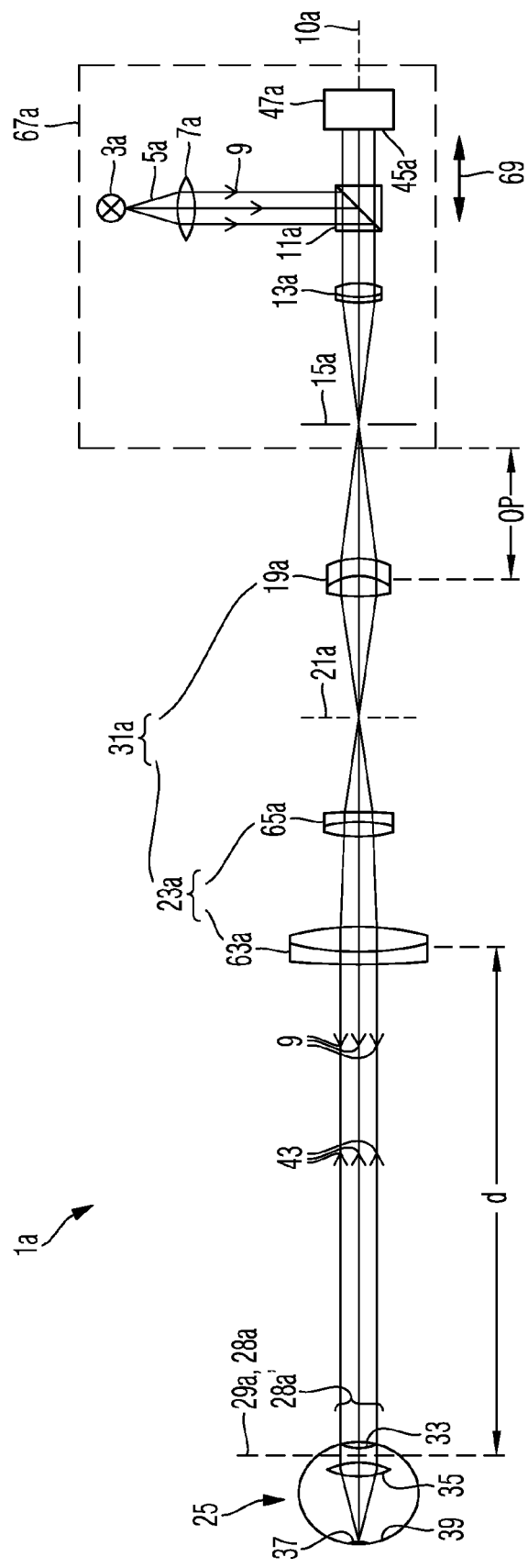
FIG. 2A schematically illustrates a further embodiment of an optical measuring system, wherein an illumination beam path or wavefront beam path, respectively, is illustrated.
Figure 2B:
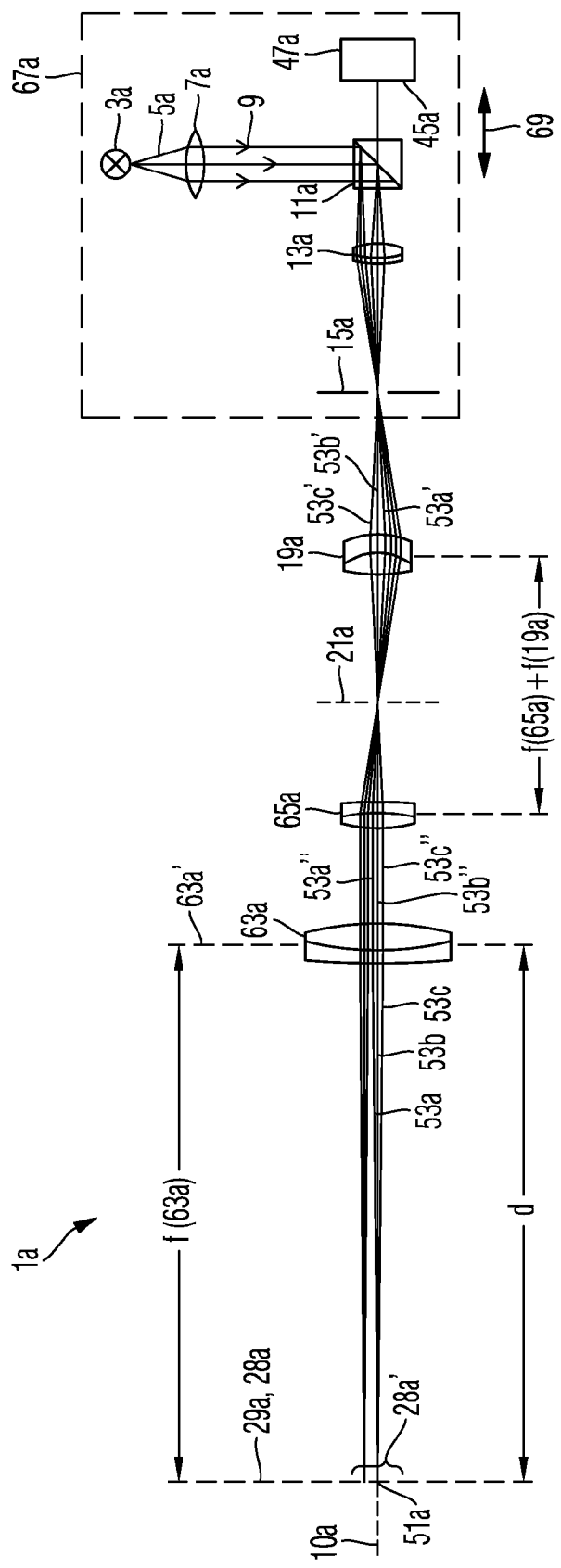
FIG. 2B chematically illustrates the embodiment, which is illustrated in FIG. 2A, wherein an object beam path is illustrated.

FIGS. 2A and 2B schematically illustrate a further embodiment 1a of an optical measuring system. Some components of the optical measuring system 1a are analog to components of the optical measuring system 1, which is illustrated in FIGS. 1A, 1B and 1C. Thereby, for a detailed description of these components, it is referred to the corresponding description of the embodiment 1. For example, cemented elements 19a and 13a of the embodiment 1a correspond to cemented elements 19 and 13 of the embodiment 1. Furthermore, light source 3, collimating optics 7 and wavefront sensor 47 of the embodiment 1 correspond to light source 3a, collimating optics 7a and wavefront sensor 47a of the embodiment 1a.

Unlike embodiment 1 of the optical measuring system, which is illustrated in FIGS. 1A, 1B and 1C, and which comprises cemented element 23, the embodiment 1a, which is illustrated in FIGS. 2A and 2B comprises a lens group 23a which consists of lens system 63a and lens system 65a. Furthermore, embodiment 1a does not comprise a reflector 17 or a corner cube 17, respectively, as is the case for embodiment 1. Rather, aperture 15a, cemented element 13a, beam splitter 11a, collimating optics 7a, light source 3a and the wavefront sensor 47a are arranged at a fixed position relative to each other and may together be displaceable in a direction along the optical axis 10a of the measuring system 1a. This is illustrated by the dashed box 67a, which is displaceable along directions, which are indicated by the double arrow 69. As is explained with reference to embodiment 1, which is illustrated in FIGS. 1A, 1B and 1C, a variation of the optical path between cemented elements 19 and 13 or 19a and 13a, respectively, of the measuring light, which is incident on the object region 28', as well as measuring light 43, which emanate from the object region 28' allows a compensation of a spherical aberration of an eye under inspection 25. The compensation effects the illumination as well as the analysis of the wavefront of the measuring light, which exits the eye 25. Thereby, a dynamic measuring range of the wavefront sensor 47 may be extended.

Instead of providing a displaceable unit 67a for this purpose in the embodiment, there may be provided an arrangement by using a reflector 17 or a corner cube 17, respectively, as is illustrated in FIGS. 1A and 1B in a corresponding way. Accordingly, the embodiment 1 of the optical measuring system, as illustrated in FIGS. 1A, 1B and 1C may not comprise a reflector 17. Instead, the components aperture 15, cemented element 13, beam splitter 11, collimating optics 7, light source 3 and wavefront sensor 47 may be supported at a fixed position relative to each other and are designed to be displaceable together along the optical axis 10, such as it is illustrated in FIGS. 2A and 2B in a corresponding way. These components also may be designed not to be displaceable. In case these components are not displaceable, there is provided a wavefront sensor 47 having a large dynamic range since in this case a pre-compensation is not possible when eyes having a spherical aberration are inspected.

In the object region 28' in the object plane 28a within the focal plane 29a, the cornea 33 or the pupil of an eye 25 of an emmetropic eye without spherical aberration is arranged. The light 5a, which is generated by the light source 3a is transformed by collimating optics 7a into measuring light 9, which substantially consists of plane wavefronts. Measuring light 9 is incident as plane wavefront on the eye 25 after having been reflected by beam splitter 11a, having traversed cemented element 13a, having passed aperture 15a, having passed the cross-over, having traversed cemented element 19a, having passed the cross-over of the measuring light 9 in plane 21a, having traversed lens system 65a and having traversed lens system 63a. The ametropic eye, having no spherical aberration, focuses measuring light 9 onto a point 37 of the retina 39 of the eye 25. From point 37, spherical wavefronts emanate and exit the eye as measuring light 43 having plane wavefronts in the object region 28' after having traversed the vitreous body, the lens 35 and the cornea 33. Measuring light 43 traverses lens system 63a, traverses lens system 65a, traverses cemented element 19a, traverses cemented element 13a and traverses beam splitter 11a and is incident on the wavefront sensor 47a. There, the CCD detector, which is not illustrated, records distribution of light for determining a form of a wavefront of measuring light 43 which emanates from the object region 28'.

The working distance d between the object region 28' and a surface of the lens system 63a, which is located closest to the object region 28' is about three times as large as the focal length f of the first optical assembly 31a, which consists of the lens system 63a, lens system 65a and cemented element 19a. Thereby, embodiment 1a of the optical measuring system provides a sufficiently large working distance d for providing sufficient free working space for performing surgical operations.

FIG. 2B illustrates embodiment 1a of the optical measuring system, wherein an object beam path, i.e. a beam path, which emanates from object plane 28a, is illustrated for demonstrating further properties of the measuring system 1a. The pupil of the eye 25 is arranged in the object plane 28 in the illustrated example of using the optical measuring system 1a for examining the eye 25. Therefore, the object beam path corresponds to a pupil beam path. Light beams 53a, 53b and 53c, of light 43, which emanate from a focal point 51a are transformed by lens system 63a into light beams 53a", 53b" and 53c", each of which runs parallel to the optical axis 10a of the optical measuring system 1a. The focal point 51a is also located in the object region 28a'. Hence, the distance between the principal plane 63a' of the lens system 63a and the object region 28a' is equal to the focal length f (63a) of the lens system 63a. The focal length f (63a) of the lens system 63a substantially corresponds to a working distance d between the object region 28a' and a surface of the lens system 63a, which is located closest to the object region 28a'. Lens system 65a and cemented element 19a are arranged at a distance along the optical axis 10, which correspond to a sum of their focal length, i.e. f(65a)+f(19a). Thereby, the lens system 65a and the cemented element 19a form a so-called Kepler telescope. The Kepler telescope is an example of an afocal system, which transforms incident parallel light beams into outgoing parallel light beams. Accordingly, the parallel light beams 53a", 53b" and 53c" are transformed by lens system 65a and cemented element 19a into parallel light beams 53a', 53b' and 53c'. After light beams 53a', 53b' and 53c' have traversed cemented element 13a, they are focused onto the entry region 45a of the wavefront sensor 47a. Thereby, the object region 28a' is imaged onto the entry region 45a of the wavefront sensor. Since the light beams between the cemented element 19a and the cemented element 13a are parallel, such an imaging is independent from a modification of the optical path of the measuring light between the cemented elements 19a and 13a. Such a modification is achieved by displacing the system 67a, along directions, which are indicated by arrow 69.

Figure 3:
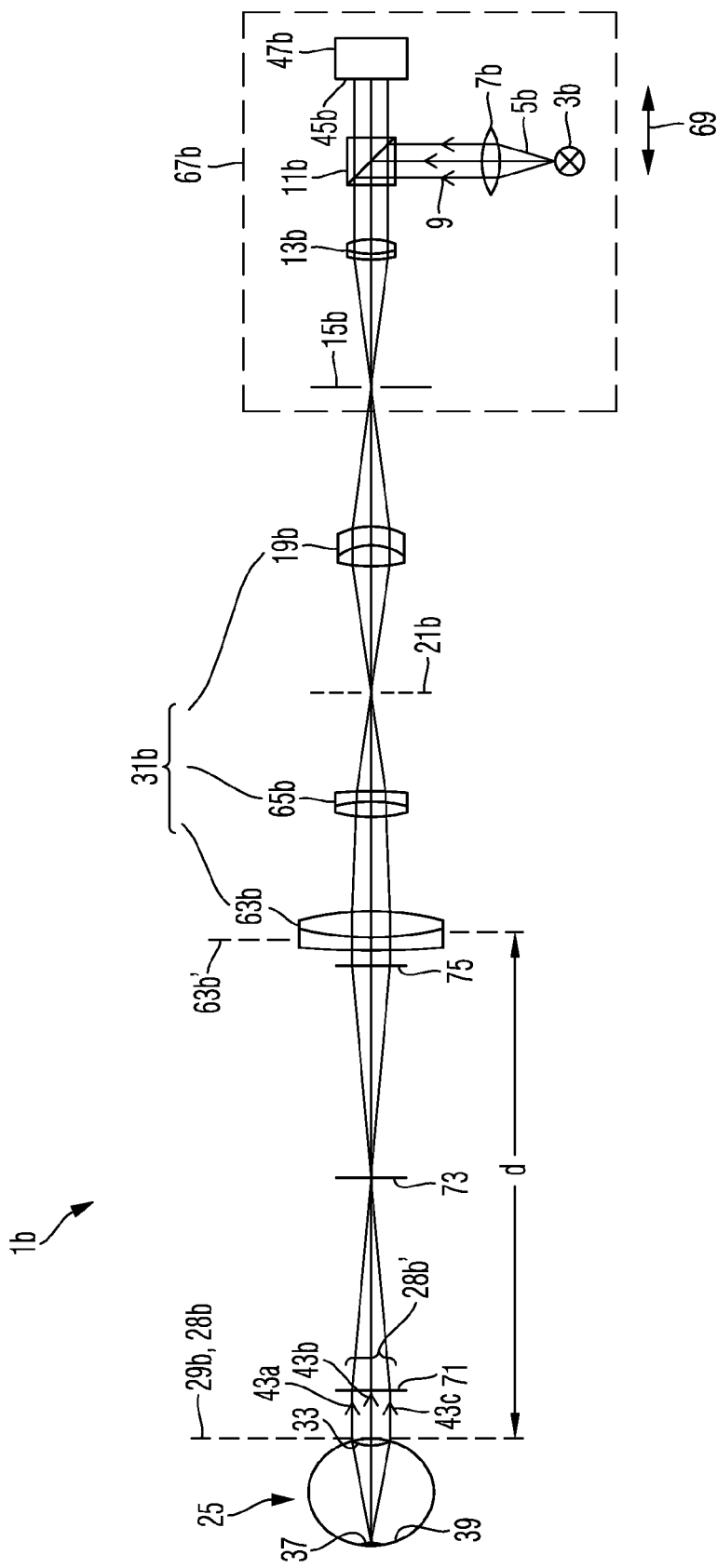
FIG. 3 chematically illustrates a further embodiment of an optical measuring system.

FIG. 3 shows a further embodiment 1b of an optical measuring system. The structure and the orientation of the elements 63b, 65b, 19b, 13b, 11b, 7b, 3b and 47b, relative to each other, substantially correspond to the structure and the relative arrangement of the elements 63a, 65a, 19a, 13a, 11a, 7a, 3a and 47a, respectively, which are illustrated in FIGS. 2A and 2B. Compared to the embodiment illustrated and described so far, the optical measuring system 1b comprises further lens elements 71, 73 and 75, which are arranged in this order between the object region 28b' in the focal plane 29b of the first optical assembly 31b which consists of the lens system 63b, the lens system 65b and the cemented element 19b. The lens element 71 comprises a focal length of 40 mm, the lens element 73 comprises a focal length of 18.5 mm and the lens element 75 comprises a focal length of 75 mm. These lens elements 71, 73 and 75 are arranged to inspect an aphakic eye 25, i.e. an eye, the lens of which has been removed and which is therefore omitted in FIG. 3. Light beams 43a, 43b and 43c are illustrated, which diverge from a point 37 of the retina 39 of the eye 25 and exit the eye 25. In the illustrated embodiment, the aphakic eye has 19 diopters. The divergent light beams 43a, 43b and 43c, which emanate from the object region 28b' and which represent spherical wavefronts, are imaged by the optical imaging system of the optical measuring system 1b as parallel wavefronts onto the entry region 45b of the wavefront sensor. Thereby, it is possible by inserting the lens elements 71, 73 and 75, to further increase the dynamic measuring range of the wavefront sensor 47, such that even aphakic eyes may be inspected in view of spherical and non-spherical aberrations. Lens elements 71, 73 and 75 may also be provided in embodiments, which are illustrated in FIGS. 1A, 1B, 1C, 2A and 2B.

Figure 4:
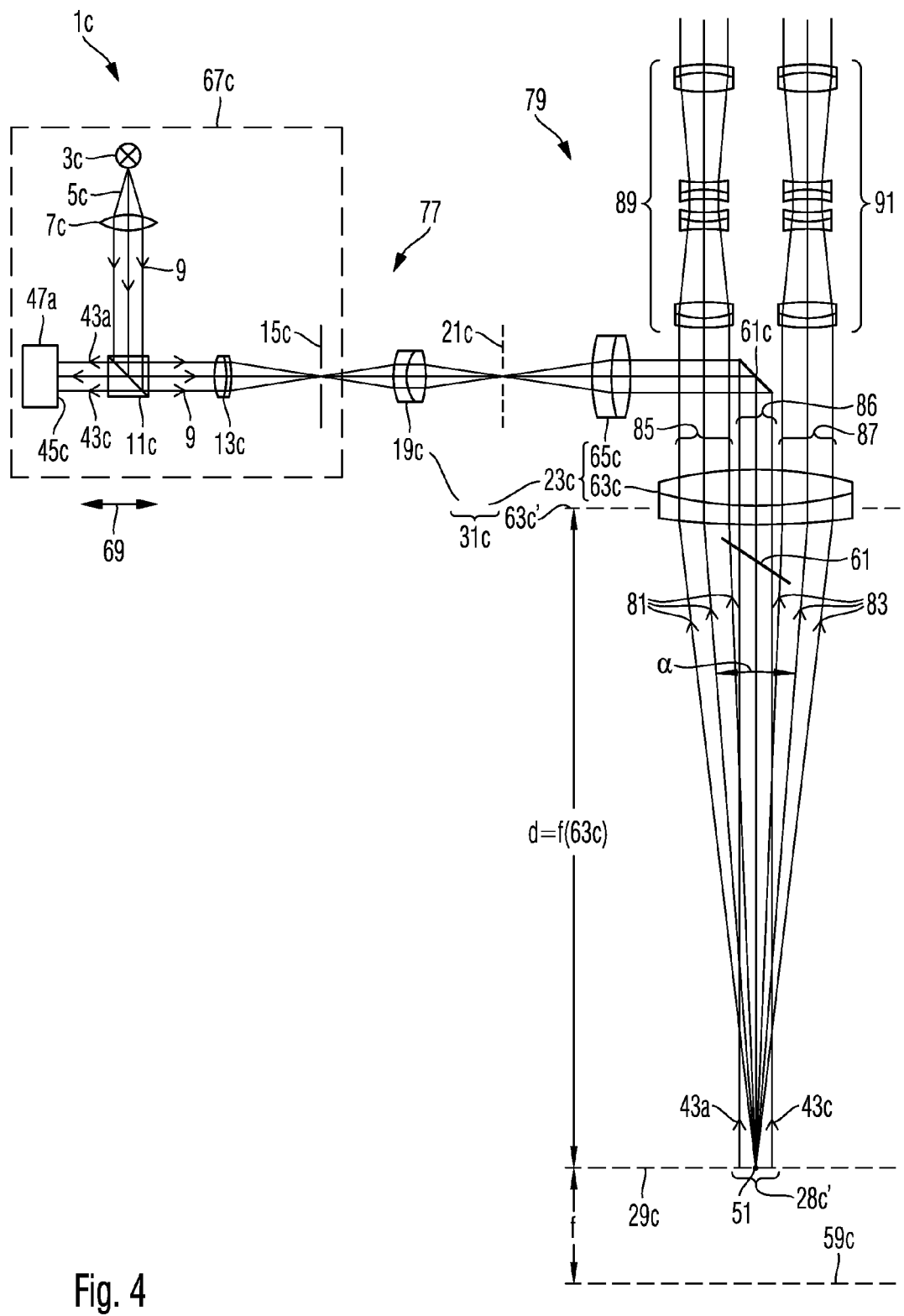
FIG. 4 schematically illustrates a further embodiment of an optical measuring system.

FIG. 4 illustrates a further embodiment 1c of an optical measuring system. The optical measuring system 1c comprises a wavefront analysis system 77 and an optical microscopy system 79. Many of the components of the wavefront analysis system 77 have a similar structure and a similar relative orientation as the optical measuring system 1a, as shown in FIGS. 2A and 2B. A detailed description of these components is therefore omitted. The lens system 63a of the optical measuring system 1a is also an objective lens 63c of the optical microscopy system 79 in the optical measuring system 1c. In the embodiment, shown in FIG. 4, the objective lens 63c has a diameter of 53 mm. Light beams 43a, 43b and 43c, which emanate as parallel beams from the object region 28c' in the focal plane 29c of the first optical assembly 31c, which consists of the lens system 19c, the lens system 65c and the objective lens 63c, and which therefore form plane wavefronts, are incident on the wavefront sensor 47c as plane wavefronts after having traversed the first optical assembly 31c, the cemented element 13c and the beam splitter 11c. Parallel light beams, which emanate from the object region 28c' and which therefore do not represent plane wavefronts, are incident on the wavefront sensor 47c as non-plane wavefronts. As described above, a form of such non-plane wavefronts may be determined by detecting an intensity distribution by the wavefront sensor 47c and by a subsequent analysis.

Furthermore, the optical measuring system 1c allows to acquire microscopic images of the object region 28c'. From a point 51 in the object region 28c' in the focal plane 29c of the first optical assembly 31c (and the objective lens 63c), light beams 81 and 83 emanate. Light beams 81 and 83 form a stereo angle α. Light beams 81 traverse a region 85 of the objective lens 63c and light beams 83 traverse a region 87 of the objective lens 63c and thereafter propagate as parallel light beams. Then, light beams 81 traverse a zoom system 89 and light beams 83 traverse a zoom system 91. Downstream of the objective lens, 63c, there may be located an ocular system and/or a camera for imaging the object region 28c' into an image region.

In the illustrated embodiment, the distance d between a surface, which is located closest to the object region 28c' of the objective lens 63c and the object region 28c' amounts to 20 cm. In the illustrated embodiment, this distance corresponds to the focal length f(63c) of the objective lens. Further embodiments comprise an objective lens having a focal length of 15 cm or 25 cm. A focal length f of the optical assembly 31c, which consists of the lens system 19c, lens system 65c and the objective lens 63c, amounts to about 70 mm in the illustrated embodiment. Thereby, a sufficiently large working space is provided for conducting a surgical operation, wherein the focal length f is much smaller.

In the embodiment 1c of the optical measuring system, which is illustrated in FIG. 4, light rays 43a, 43b and 43c, which are used for an analysis of the wavefront, traverse the objective lens 63c of the optical microscopy system 79. The objective lens 63c is traversed in a region 86 of the objective lens 63c, which is different from the regions 85 and 87 through which light beams 81 and 83 pass, which are used for microscopic imaging. Light beams 43a, 43b and 43c, which are used for an analysis of the wavefront, are decoupled from further components of the optical microscopy system 79 by folding mirror 61c.

Figure 5A:
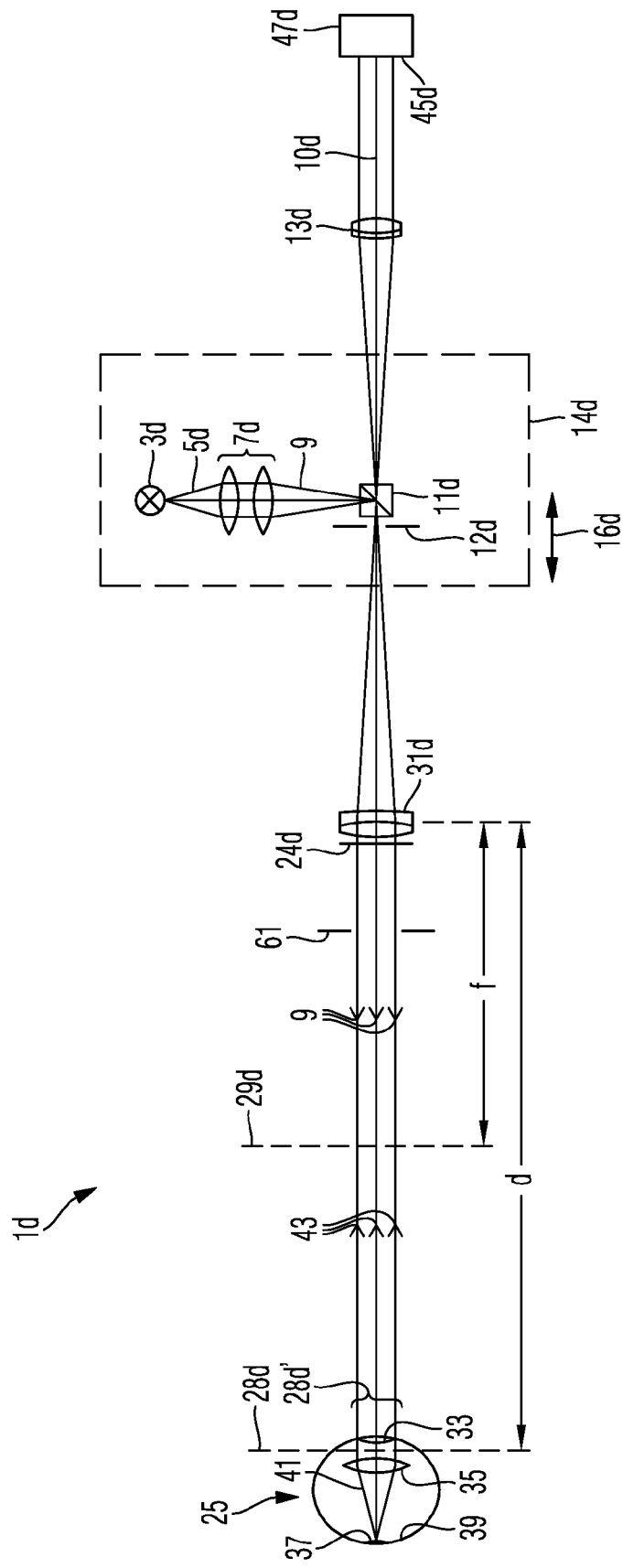
FIG. 5A schematically illustrates a further embodiment of an optical measuring system, wherein an illumination beam path or wavefront beam path, respectively, is illustrated.
Figure 5B:
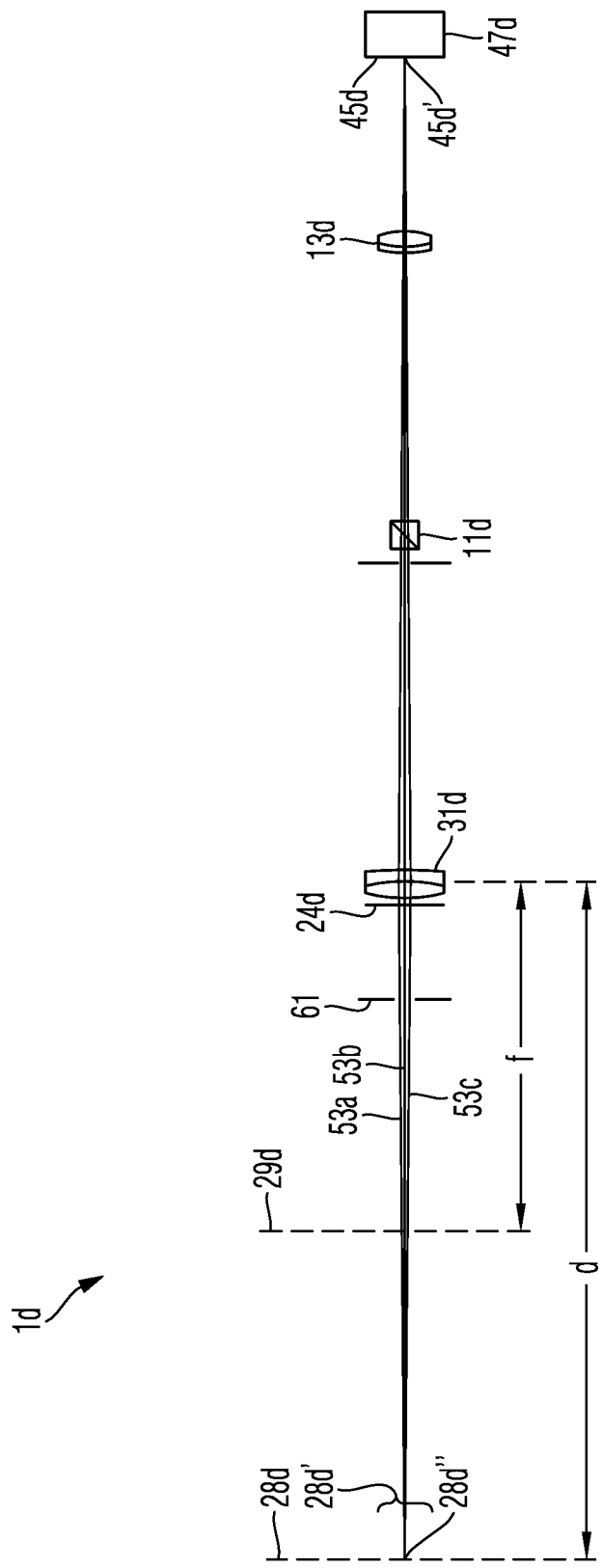
FIG. 5B schematically illustrates the embodiment, which is illustrated in FIG. 5A, wherein an object beam path is illustrated.

As an alternative to this method of decoupling, light beams 43a, 43b and 43c may be decoupled between the object region 28c' and the objective lens 63c of the optical microscopy system 79 through a folding mirror 61, which is indicated by a dashed line. Thereby, embodiment 1 of an optical measuring system, which is illustrated in FIGS. 1A, 1B and 1C, may be combined with the optical microscopy system 79 or with the embodiment 1d, which is illustrated in FIGS. 5A and 5B. This is illustrated in FIGS. 1A, 1B, 5A and 5B by folding mirror 61.

Instead of simultaneously displacing the components, which are surrounded by box 67c of the wavefront analysis system 77, the optical path between lens system 19c and cemented element 13c may be varied by providing a displaceable corner cube 17, such as is illustrated in FIGS. 1A and 1B. This way of pre-compensation of a spherical aberration of an eye under inspection may be used in combination with the decoupling of measuring light 47 with folding mirror 61c as well as the decoupling of the measuring light 43 by using folding mirror 61.

The optical measuring system 1c provides to the surgeon a microscopic image of the anterior chamber of the eye and at the same time allows to analyze a wavefront of measuring light which is emitted from the eye. Thereby, an accurate measurement of a refraction is possible by using the wavefront sensor. Due to the large working space, the wavefront analysis system does not have to be removed during the surgical operation and does not have to be inserted in case it is needed. Thereby the handling is significantly simplified and the wavefront analysis system does not need to be pivotably supported.

The object region 28c' is also located in the focal plane of the objective lens 63c. Downstream of the objective lens 63c, light beams 81 and 83 which emanate from a point 51 of the object region 28c', are parallel, which result in further advantages for the subsequent components and the microscopic imaging. In the wavefront analysis system 77 of the optical measuring system 1c, further lens elements 71, 73 and 75 may be provided in an analogy to the embodiment 1b of an optical measuring system, which is illustrated in FIG. 3, for analyzing wavefronts, which exit from an aphakic eye. Therefore, it is possible, to inspect eyes having spherical aberrations of 14 diopters, 19 diopters, 24 diopters and values therebetween. In case the lens elements 71, 73 and 75 are not provided, eyes having spherical aberrations of at least in the range between −5 dpt and +5 dpt may be inspected by varying the optical path between elements 13 and 19, 13a and 19a, or 13c and 19c, respectively.

The Kepler telescope, which is formed by the lens system 65a and the cemented element 19a, which is illustrated in FIGS. 2A and 2B, may be replaced by a Galilei telescope or another afocal system.

According to an embodiment, the entry region of the wavefront sensor has an extent of 6.34 mm*6.34 mm. In alternative embodiments, other extents may be provided. The light source 3, 3a, 3b and 3c, respectively, typically comprises a superluminescence diode and acts as a point light source. Also, the optical measuring system 1c may be designed such that an optical path is variable for a pre-compensation of a spherical aberration. Optical elements, which interact with a polarization of light such as for example quarter wave plates or a beam splitter, which is configured as a polarization beam splitter, may be used for separating the reflected light, which is generated at optical surfaces from measuring light, which emanates from the illumination spot 37 on the retina 39.

FIGS. 5A and 5B schematically illustrate a further embodiment of an optical measuring system 1d. Again, in FIG. 5A, an illumination beam path or a wavefront beam path is illustrated and in FIG. 5B, an object beam path is illustrated. The optical measuring system 1d comprises a first optical assembly 31d, which in this embodiment is a cemented element, a second optical assembly 13d which in this embodiment is a cemented element and a wavefront sensor 47d.

For illuminating the eye 25, the optical measuring system 1d further comprises a light source 3d, which emanates light 5d. Light 5d is converted by beam shaping optics 7d into convergent measuring light 9 and focused into the region of the aperture 12d after being reflected at the beam splitter 11d. In case an emmetropic eye is inspected, aperture 12d is arranged in a focal plane of cemented element 31d. After having traversed the cemented element 31d, measuring light 9 substantially comprises plane wavefronts which are incident on the eye 25. After having traversed the cornea 33, the natural lens 35, measuring light 9 is focused onto a point 37 of the retina 39.

Light 41 emanates from point 37 and form measuring light 43 after having traversed the natural lens 35 and the cornea 33. In case of an emmetropic eye, measuring light 43 substantially consists of plane wavefronts. The pupil of the human eye is arranged in the object plane 28d in the object region 28d'. The distance between the object plane 28d and the cemented element 31d is denoted as distance d and the focal length of the cemented element 31d is denoted as distance f in FIG. 5A. Measuring light 43, which emanates from the object region 28d' traverses cemented element 31d, passes the crossover in a plane of the aperture 12d, traverses beam splitter 11d, traverses cemented element 13d and impinges onto the entry region 45d of the wavefront sensor 47d as plane wavefronts in case of an emmetropic eye.

Cemented element 31d and cemented element 13d form an afocal system, such as for example a Kepler system. For achieving this, the cemented element 31d and the cemented element 13d are arranged at a distance along the optical axis 10d, wherein the distance corresponds to the sum of the focal length of the cemented element 31d and the cemented element 13d.

Through displacing of the component along the optical axis 10d which are surrounded by box 14d, as indicated by double arrow 16d, (i.e. the light source 3d, the beam shaping optics 7d, the beam splitter 11d and the aperture 12d), it is possible even in case an eye having a spherical aberration is investigated, to generate an illumination spot 37 which has a small extent on the retina 39 of the eye 25. In this case, measuring light 43, which emanates from the object region 28d' does not consists of substantially plane wavefronts. Therefore, it is possible for the wavefront sensor 47d, which is used in embodiment 1d, to measure wavefronts having a comparatively small curvature.

FIG. 5B illustrates an object beam path of the optical measuring system 1d. Light beams, which emanate from a point 28d'' in the object region 28d' in the object plane 28d traverse cemented element 31d, beam splitter 11d and cemented element 13d and impinge onto a point 45d' in the entry region of the wavefront sensor 47d. It is obvious that the distance d between cemented element 31d and the object plane 28d is much larger than the focal length f of the cemented element 31d.

The optical measuring system 1d may comprise a folding mirror 61, which allows to combine the optical measuring system 1d with an optical microscopy system 79, as illustrated in FIG. 4. In FIG. 4, the position of the folding mirror 61 is schematically indicated.

Figure 6:
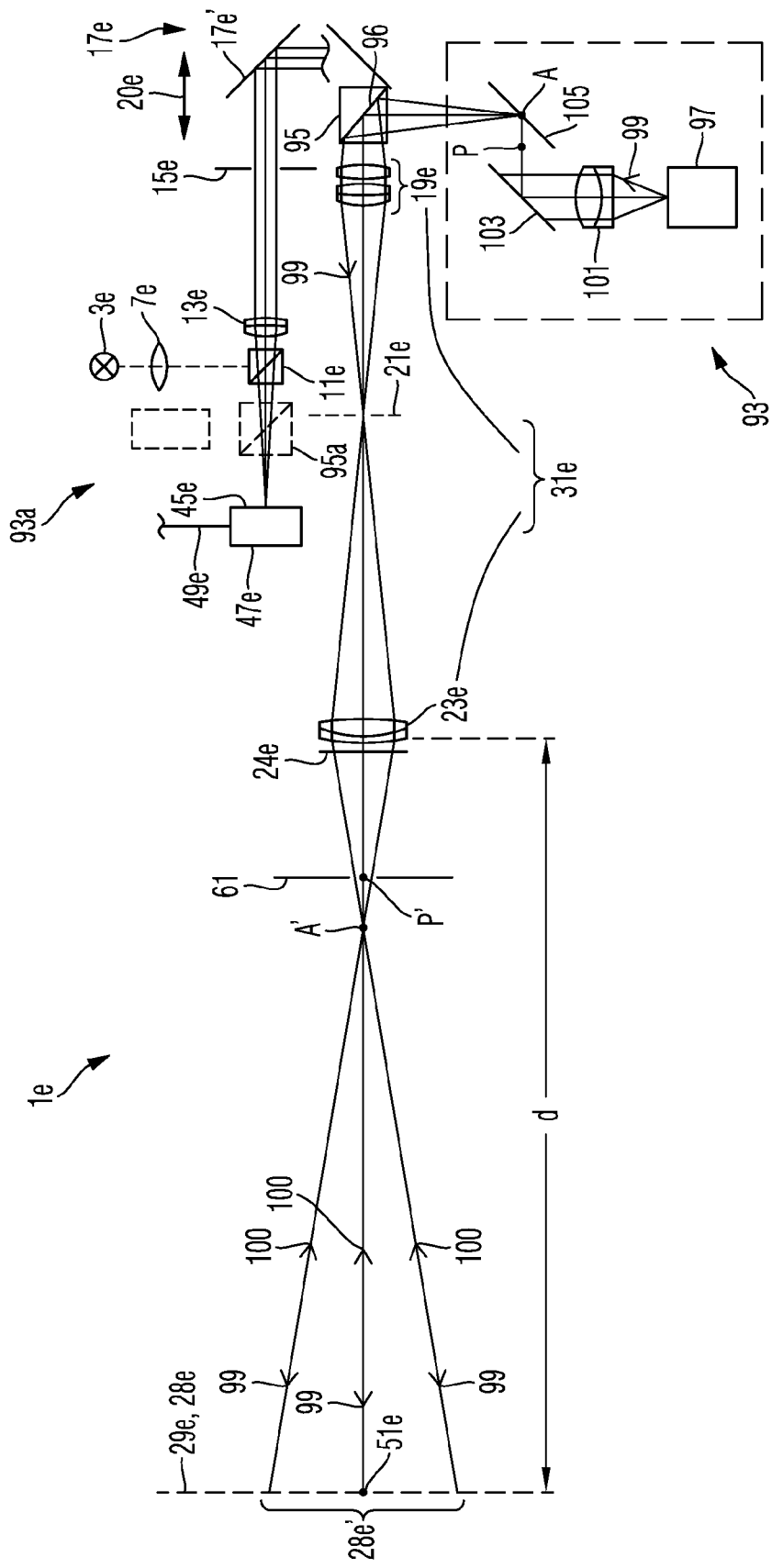
FIG. 6 shows an optical measuring system according to a further embodiment, wherein an OCT beam path is illustrated.

FIG. 6 schematically illustrates an optical measuring system 1e according to an embodiment. The optical measuring system 1e, as illustrated in FIG. 6, is configured to inspect an object region 28e' by an analysis of a wavefront which emanates from an object region and by optical coherence tomography (OCT). To this effect, the measuring system 1e, as illustrated in FIG. 6, comprises in addition to the measuring system 1, as illustrated in FIGS. 1A and 1B, an OCT system 93 and an OCT beam splitter 95. The OCT system 93 comprises OCT components 97, which comprise an OCT light source for generating OCT measuring light 99, an optical coupler for dividing and combining OCT measuring light, a reference mirror, a spectrometer, a position sensitive detector and an analysis system.

The OCT light source emits OCT measuring light 99 which traverses collimating optics 101 and enters as collimated OCT measuring light beam a scanner, which comprises two scanning mirrors 103 and 105. The scanning mirrors 103, 105 are pivotable about axes, which are oriented perpendicular to each other for scanning OCT measuring light 99 over the object region 28e'. For illustrative purposes, the elements 97, 101 and 103 are illustrated in FIG. 6 as being tilted about the connecting line between the two scanning mirrors 103 and 105. The OCT measuring light 99 may comprise as a major part wavelengths of light between 1290 nm and 1330 nm.

FIG. 6 shows in an exemplary way three light beams of OCT measuring light which are reflected at a point A of the scanning mirror 105 when the scanning mirror is positioned at three different pivoting positions which are obtained by pivoting the pivoting mirror about a pivoting axis which is oriented perpendicular to the paper plane and which intersects point A. The light beams of OCT measuring light 99 are incident on the OCT beam splitter 95 which comprises a dichroic mirror 96. The dichroic mirror 96 comprises layers which are deposited on a mirror surface of the dichroic mirror 96, wherein the layers have different dielectric properties for reflecting the incident OCT measuring light 99 with a high effectivity and to transmit only a small portion, such as less than 30%. The OCT measuring light 99 traverses the lens 19e after having been reflected at the dichroic mirror 96. For example, the lens 19e may be designed as a cemented element and an additional individual lens. Then, the OCT measuring light 99 traverses cemented element 23e. Cemented element 23e and lens 19e form the first optical assembly 31e. The first optical assembly 31e images the point A in the center of the scanning mirror 105 onto a point A' between the first optical assembly 31e and the object region 28e', in which the focal point 51e of the first optical assembly 31e is located. Similarly, a point P in the center of the connecting line between the scanning mirror 103 and the scanning mirror 105 is imaged by the first optical assembly 31e onto a point P'. At this position, an optional folding mirror 61 may be located for deflecting OCT measuring light 99, which propagates towards the object region 28e' and OCT measuring light, which returns from the object region 28e'. This may be advantageous in case the optical measuring system 1e is used in combination with an optical microscope. In this case a folding mirror 61 may be arranged in the beam path of the microscope between the main objective lens of the microscope and the object region 28e'.

In such a case, it may be advantageous that the optical measuring system 1e images the point P onto the point P', which is located on the folding mirror 61, since for different pivoting positions of the mirrors 103, 105, a walk-off of the point P' from the center of the folding mirror 61 is minimized. Hence, it is possible to design the folding mirror 61 compact in size such that vignetting of the beam path of the microscope is prevented. In order to achieve this, all scanning mirrors of a scanner (in this case the scanning mirrors 103 and 105) have to be arranged as close as possible to the point P and the folding mirror 61 has to be located as close as possible to the point P'.

The three light beams of OCT measuring light which correspond to three different pivoting positions of the scanning mirror 105 are incident at the three different points within the object region 28' at which they interact with the object, which is arranged in the object region 28e'. In FIG. 6, there are shown only three scanning points. However, by continuously pivoting the scanning mirrors 103, 105 the entire object region 28e' is scanned.

OCT measuring light, which emanates from the object region 28e' has been reflected at different layers within the object and thereby contains structural information of the object under inspection. The reflected OCT measuring light 100 traverses cemented element 23e, lens 19e and a major part is reflected at the dichroic mirror 96 of the OCT beam splitter 95. After further reflections at the scanning mirrors 105, 103, the returning OCT measuring light traverses collimating optics 101 and enters an optical fiber of the OCT components 97, which is not illustrated. Then, the returning OCT measuring light is superimposed on reference light and spectrally dispersed by a spectrometer and detected by a position sensitive detector. A spectrum of the returning OCT measuring light, which is interferometrically superimposed on reference light, is processed for obtaining structural information from the lateral object region 28e' of the object under inspection along a depth direction, i.e. perpendicular to the object plane 28e.

Such as the embodiment 1 of an optical measuring system, as illustrated in FIGS. 1A and 1B, also the optical measuring system 1e, as illustrated in FIG. 6, comprises components for analyzing a wavefront, as described above. For simplicity of illustration, in FIG. 6, a beam path of measuring light 9, which is guided towards the object region 28e' through cemented element 13e, lens 19e and cemented element 23e, as well as returning measuring light 43 are not illustrated. These beam paths are illustrated in FIGS. 1A and 1B from which it may be seen that also in the embodiment of an optical measuring system 1e, which is illustrated in FIG. 6, the object region 28', which may comprise the focal point 51e of the first optical assembly 31e is imaged onto the entry region 45e of the Hartmann-Shack sensor 47e.

Therefore, the embodiment 1e allows to simultaneously inspect the object region 28' by analyzing wavefronts, which emanate from this region and by acquiring OCT structural data. The wavefront light source 3e may be configured such that a central portion of measuring light which is generated by light source 3e is located within a range of wavelengths of about 830 nm to 870 nm. The OCT beam splitter 95, or its dichroic mirror 96 is designed such that a substantial portion of light of a wavelength range of about 830 nm to 870 nm is transmitted. Thereby, it is possible to separate the OCT measuring light from the measuring light for inspecting a wavefront in order to reduce disturbances.

According to a further embodiment, no reflector 17e is provided between lens 19e and cemented element 13e, such that a beam path of measuring light 9, 43 which is used for an analysis of the wavefront propagates in a straight line along an optical axis of cemented elements 19e, 23e, i.e. an optical axis of the first optical assembly 31e, without being deflected.

According to a further embodiment, the OCT beam splitter 95 may be arranged between the second optical assembly 13e and the Hartmann-Shack sensor 45e, instead of being located between the first optical assembly 31e and the second optical assembly 13e. This is indicated by the dashed box 95a. Accordingly, the OCT system 93 is illustrated as an alternative with a dashed box having reference sign 93a. This embodiment is advantageous in case structural information is to be obtained from the posterior portion of the eye by using the OCT system. This arrangement of the OCT beam splitter 95a or the OCT system 93a may be used when the optical measuring system does not have a reflector 17e, as described above.

Figure 7:
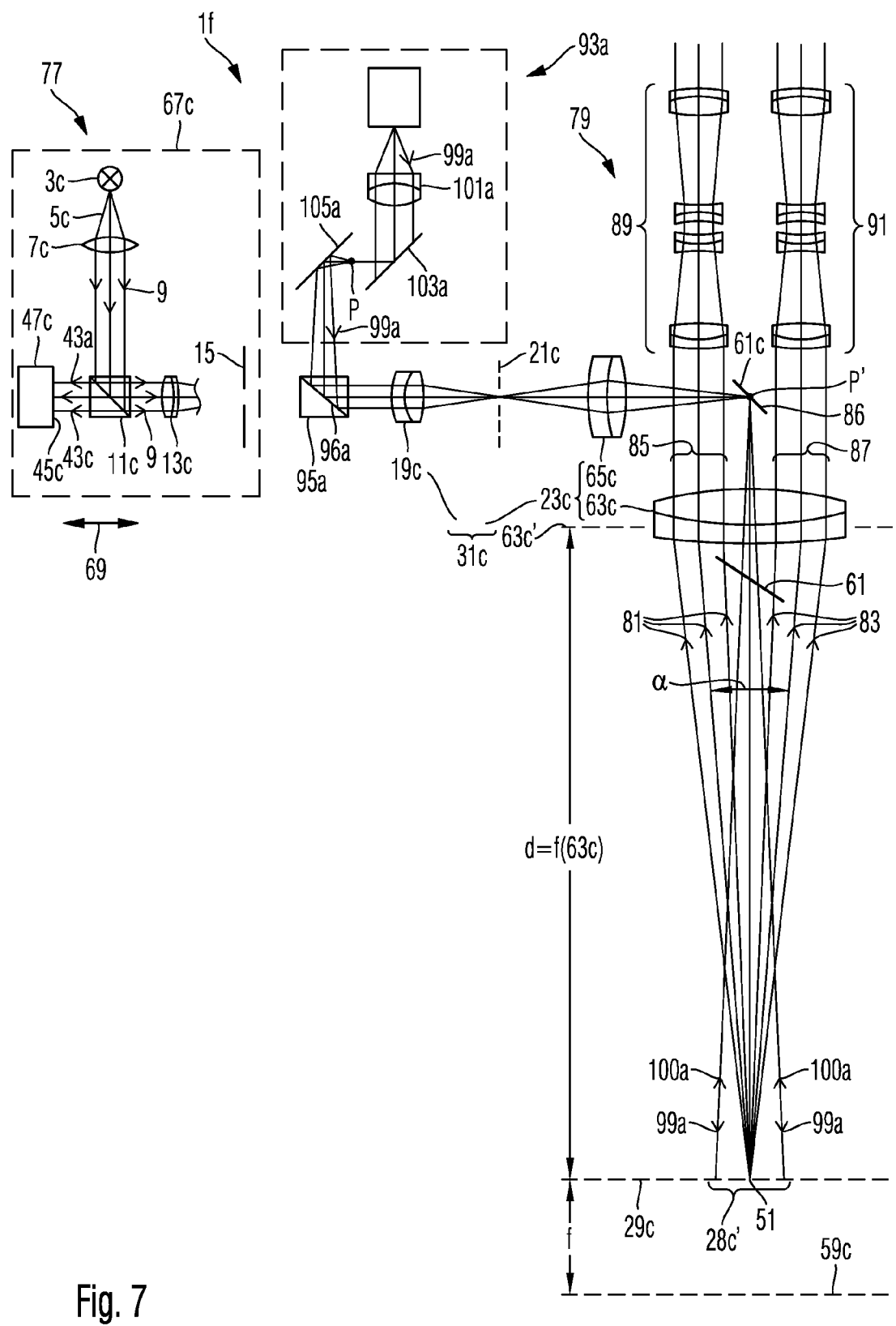
FIG. 7 shows an optical measuring system according to a further embodiment, wherein an OCT beam path is illustrated.

FIG. 7 schematically illustrates an optical measuring system if according to a further embodiment. The optical measuring system 1f, as illustrated in FIG. 7, is designed in a similar way as the optical measuring system 1c, as illustrated in FIG. 4, in so far as the optical measuring system if also comprises components 67c of a wavefront analysis system 77 as well as a microscopy system 79. The microscopy system 79 comprises an objective lens 63c for imaging the object region 28c', which is located in a focal plane 29c, after having traversed zoom systems 89, 91. Also, the wavefront analysis system 77 is designed such that wavefronts, which emanate from the object region 28c' or which traverse the object region 28c' are inspectable in view of their form, as has been described with reference to FIG. 4.

In addition to the functionalities of the optical measuring system 1c, as illustrated in FIG. 4, the optical measuring system 1f, as illustrated in FIG. 7, allows to inspect the structure of an object region 28c' along a depth direction, i.e. perpendicular to the focal plane 29c by using the OCT system 93a. To this effect, the OCT system 93a comprises similar components as the OCT system 93, which is illustrated in FIG. 6.

In FIG. 7, there is schematically illustrated a beam path of the OCT measuring light 99a for three different pivoting positions of the scanner, which consists of the scanning mirrors 103a, 105a. For simplicity of illustration, OCT measuring light 99a which emanates in three different directions from the point P between the scanning mirrors 103a, 105a is illustrated. Alternatively, at this point P, a center of a 3D-scanner may be arranged. In case a scanner comprises more than one mirroring surface, the point P is advantageously arranged such that distances to mirror surfaces of the scanner are minimized.

Light beams of OCT measuring light 99, which emanate from the point P, are reflected at the scanning mirror 105a, are reflected at dichroic mirror 96a to a major part and traverse the afocal system, which consists of the cemented element 19c and the cemented element 65c, and is imaged onto the point P', which is arranged in the center of the folding mirror 61c. Point P is imaged by the cemented element 19c, i.e. the second optical subassembly of the first optical assembly 31c and through cemented element 65c, i.e. the second lens group of the first optical subassembly of the first optical assembly onto the point P' which is located at the center of the folding mirror 61c. Hence, for different pivoting positions of the scanner, which consists of scanning mirrors 105a, 103a, there is a minimal walk-off of the point P'. In case of an ideally arranged 3D-scanner having only one reflecting surface, there is expected to be no beam walk-off. This allows to design the folding mirror 61c compact in size, such that beam paths of the microscope 81 and 83 can pass the folding mirror 61 and enter the respective zoom system of the stereo microscope system 79.

As an alternative to the arrangement of the OCT beam splitter 95a and the OCT system 93a, as illustrated in FIG. 7, these components or at least the OCT beam splitter 95a may be arranged between cemented element 65c and the folding mirror 61c.

As an alternative to the embodiments, which are illustrated in FIGS. 6 and 7, the OCT beam splitter 95, 95a or the dichroic mirror 96, 96a may be designed such that OCT measuring light 99, 99a may be transmitted with a higher effectivity than reflected. They further may be designed such that measuring light 9, which is used for the measurement of the wavefront is reflected with a higher effectivity than transmitted. Hence, in alternative embodiments, the spatial arrangement of the wavefront analysis system 77 and the OCT system 93, 93a may be interchanged.

According to further embodiments, a range of wavelengths, which comprises 70% of a total intensity of OCT measuring light may overlap with a range of wavelengths, which comprises 70% of a total intensity of measuring light for inspecting the wavefront. Thereby, light of the same wavelength range may be used for inspecting the wavefront and for inspection by using OCT light. In this case, the OCT beam splitter 95, 95a, having a dichroic mirror 96, 96a is not necessary. In this case, it is advantageous to successively conduct a measurement for determining the wavefront and a measurement for determining the structure by using OCT. Thereby, an interference is prevented. However, it is also possible to conduct both measurements simultaneously. Optical elements having a polarization effect, such as quarter wave plates may be inserted into the beam path. For example, the elements 11, 11a, 11b, 11c, 11d, 11e may be configured as a polarization beam splitter.

According to further embodiments, the light beam of OCT measuring light 99 is not focused onto the object region 28c', 28e' but focused onto a region, which is located deeper, such as onto the retina of the eye under inspection.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. Measuring system for ophthalmic surgery, comprising:
   a wavefront sensor for characterizing a form of a wavefront of a measuring light in an entry region of the wavefront sensor; and imaging optics comprising a first optical assembly and a second optical assembly for imaging an object region into the entry region of the wavefront sensor by using measuring light, wherein the following relation holds: $1.1*f \leq d$, wherein f denotes a focal length of the first optical assembly; and wherein d denotes a distance between the object region and the first optical assembly.

2. The measuring system for ophthalmic surgery according to claim 1, wherein the following relation holds: $1.5* \leq d$.

3. The measuring system for ophthalmic surgery according to claim 1, wherein the following relation holds: $d \geq 150$ mm.

4. The measuring system for ophthalmic surgery according to claim 1, wherein at least one of the first optical assembly or the second optical assembly is a refractive optical assembly or a lens group.

5. The measuring system for ophthalmic surgery according to claim 1, further comprising a third optical assembly which is arranged and designed for imaging the object region along a microscope beam path onto an image region, wherein the image region is different from the entry region of the wavefront sensor.

6. The measuring system for ophthalmic surgery according to claim 1, wherein the object region is located in a focal region of the first optical assembly.

7. The measuring system for ophthalmic surgery according to claim 6, wherein the first optical assembly comprises a first optical subassembly and a second optical subassembly which are arranged at a distance from each other.

8. The measuring system for ophthalmic surgery according to claim 7, wherein the following relation holds:

$d(1,2) \geq f1*d/(d-f1)$; wherein d(1,2) denotes a distance between components of the first optical subassembly and components of the second optical subassembly; and wherein f1 denotes a focal length of the first optical subassembly.

9. The measuring system for ophthalmic surgery according to claim 7, wherein the first optical subassembly comprises a first lens group or an objective lens; and wherein the first optical subassembly further comprises a second lens group, which is arranged at a distance from the first lens group.

10. The measuring system for ophthalmic surgery according to claim 9, wherein the microscope beam path traverses the first lens group of the first optical subassembly and wherein the third optical assembly comprises a zoom system.

11. The measuring system for ophthalmic surgery according to claim 9, wherein a mirror surface is arranged between the first lens group and the second lens group of the first optical subassembly in the beam path of the measuring light.

12. The measuring system for ophthalmic surgery according to claim 9, wherein the second lens group of the first optical subassembly and the second optical subassembly together form an afocal system or a Kepler telescope.

13. The measuring system for ophthalmic surgery according to claim 9, wherein the object region is arranged in a focal region of the first lens group of the first optical subassembly.

14. The measuring system for ophthalmic surgery according to claim 6, wherein an optical path, which is traversed by the measuring light along a beam path of the measuring light between the first optical assembly and the second optical assembly, is variable.

15. The measuring system for ophthalmic surgery according to claim 14, wherein the measuring system is designed such that by varying the optical path between the first optical assembly and the second optical assembly, a form of a wavefront of measuring light, emanating from an eye, which is arranged in the object region and which has an ametropia of between −5 dpt to +25 dpt, is characterizable.

16. The measuring system for ophthalmic surgery according to claim 14, further comprising a reflector for deflecting the measuring light;

wherein the reflector is displaceably arranged between the first optical assembly and the second optical assembly in the beam path of the measuring light for varying the traversed optical path of the measuring light.

17. The measuring system for ophthalmic surgery according to claim 16 wherein the reflector comprises at least two mirror surfaces which are arranged at an angle different from zero.

18. The measuring system for ophthalmic surgery according to claim 16, wherein the reflector comprises a retroreflector or a corner cube.

19. The measuring system for ophthalmic surgery according to claim 6, further comprising a beam splitter, which is arranged between the entry region of the wavefront sensor and the second optical assembly in the beam path of the measuring light.

20. The measuring system for ophthalmic surgery according to claim 6, wherein the third optical assembly comprises an objective lens and a zoom system, wherein the beam path of the measurement light is free from traversals of the objective lens and wherein a mirror surface is arranged between the object region and the first optical subassembly in the beam path of the measuring light.

21. The measuring system for ophthalmic surgery according to claim 20, wherein the object region is arranged in a focal region of the objective lens.

22. The measuring system for ophthalmic surgery according to claim 1, wherein the object region is different from a focal region of the first optical assembly.

23. The measuring system for ophthalmic surgery according to claim 22, wherein the first optical assembly and the second optical assembly form an afocal system or a Kepler telescope.

24. The measuring system for ophthalmic surgery according to claim 22, wherein a beam splitter is displaceably arranged between the first optical assembly and the second optical assembly in the beam path of the measuring light.

25. The measuring system for ophthalmic surgery according to claim 22, wherein a mirror surface is arranged between the first optical assembly and the object region.

26. The measuring system for ophthalmic surgery according to claim 1, further comprising an OCT system having an OCT light source for generating OCT measuring light, wherein an OCT beam splitter is arranged between the first optical assembly and the second optical assembly or between the second optical assembly and the entry region of the wavefront sensor in an OCT beam path of the OCT measuring light such that the OCT measuring light is guided at least through the first optical assembly for illuminating the object region.

27. The measuring system for ophthalmic surgery according to claim 26, further comprising at least one pivotable scanning mirror which is arranged between the OCT light source and the OCT beam splitter in the OCT beam path.

28. The measuring system for ophthalmic surgery according to claim 27, wherein the scanning mirror, the second lens group of the first optical subassembly and the second optical subassembly are designed and arranged such that a region, which is close to the scanning mirror, is imaged onto a region which is close to the mirror surface.

29. The measuring system for ophthalmic surgery according to claim 26, wherein at least 80% of a total intensity of the generated OCT measuring light consists of light having wavelengths of between 1280 nm and 1320 nm.

30. The measuring system for ophthalmic surgery according to claim 26, wherein the OCT beam splitter comprises a dichroic mirror, wherein a transmission of the OCT beam splitter in a wavelength range of between 800 nm and 870 nm, or is at least twice as high or at most half as high as the transmission in a wavelength range of between 1280 nm and 1340 nm.

31. The measuring system for ophthalmic surgery according to claim 26, wherein the OCT beam splitter comprises a dichroic mirror, wherein a reflectivity of the dichroic mirror in a wavelength range of between 1280 nm and 1340 nm, is at least twice as high or at most half as high as the reflectivity in a wavelength range of between 800 nm and 870 nm, or of between 820 nm and 840 nm.

32. The measuring system for ophthalmic surgery according to claim 26, wherein at least 70% of an intensity of OCT measuring light, which is incident on the OCT beam splitter, is reflected at the OCT beam splitter.

33. The measuring system for ophthalmic surgery according to claim 26, wherein at least 70% of an intensity of the measuring light, which is incident on the OCT beam splitter is transmitted through the OCT beam splitter.

34. The measuring system for ophthalmic surgery according to claim 26, wherein at least 60%, of a total intensity of the measuring light consists of wavelengths, which define a wavelength range of measuring light, in which 80% of a total intensity of the OCT measuring light is located.

35. The measuring system for ophthalmic surgery according to claim 1, further comprising a wavefront light source for generating the measuring light wherein at least 80% of a total intensity of the generated measuring light consists of light having wavelengths of between 800 nm and 870 nm.

* * * * *